(12) United States Patent
Zhou et al.

(10) Patent No.: US 10,128,000 B1
(45) Date of Patent: Nov. 13, 2018

(54) COMPUTER SYSTEM AND METHOD FOR DELIVERING OPERATIONAL INTELLIGENCE FOR AMBULATORY TEAM BASED CARE AND VIRTUAL MEDICINE

(75) Inventors: Yi Zhou, Vancouver, WA (US); Daniel P. Henderson, Portland, OR (US)

(73) Assignee: Kaiser Foundation Hospitals, Oakland, CA (US)

( * ) Notice: Subject to any disclaimer, the term of this patent is extended or adjusted under 35 U.S.C. 154(b) by 649 days.

(21) Appl. No.: 13/452,742

(22) Filed: Apr. 20, 2012

Related U.S. Application Data

(63) Continuation of application No. 13/451,536, filed on Apr. 19, 2012.

(51) Int. Cl.
*G16H 10/60* (2018.01)

(52) U.S. Cl.
CPC .................................. *G16H 10/60* (2018.01)

(58) Field of Classification Search
CPC ...................................................... G16H 10/60
USPC ......................................................... 705/2–3
See application file for complete search history.

(56) References Cited

U.S. PATENT DOCUMENTS

| | | | |
|---|---|---|---|
| 6,148,339 A * | 11/2000 | Nagamatsu | H04L 41/0233 709/202 |
| 6,182,122 B1 * | 1/2001 | Berstis | G06F 17/30902 707/E17.12 |
| 6,760,727 B1 | 7/2004 | Schroeder et al. | |
| 7,016,856 B1 | 3/2006 | Wiggins | |
| 7,398,217 B2 | 7/2008 | Lewis et al. | |
| 7,630,371 B2 * | 12/2009 | Hernandez et al. | 370/392 |
| 7,657,445 B1 | 2/2010 | Goux | |
| 7,716,066 B2 | 5/2010 | Rosow et al. | |
| 7,716,072 B1 | 5/2010 | Green, Jr. et al. | |
| 7,720,695 B2 | 5/2010 | Rosow et al. | |
| 7,734,479 B2 | 6/2010 | Rosow et al. | |
| 7,774,215 B2 | 8/2010 | Rosow et al. | |
| 7,890,347 B2 | 2/2011 | Rosow et al. | |
| 7,953,610 B2 | 5/2011 | Rosow et al. | |
| RE42,508 E | 6/2011 | Lewis et al. | |
| 7,979,294 B2 | 7/2011 | Larsen et al. | |

(Continued)

FOREIGN PATENT DOCUMENTS

WO      WO2012006517 A2 *    1/2012    ............. G06Q 50/00

OTHER PUBLICATIONS

U.S. Appl. No. 13/452,199, filed Apr. 20, 2012, Zhou et al.
U.S. Appl. No. 13/452,604, filed Apr. 20, 2012, Zhou et al.

*Primary Examiner* — Eliza A Lam
(74) *Attorney, Agent, or Firm* — Mauriel Kapouytian Woods LLP; Lana Akopyan; Michael Mauriel

(57) ABSTRACT

Various structures and methods are disclosed related to a computer system for delivering data for operational intelligence in support of optimizing health care delivery. Particular embodiments selectively extract various data sets for operational support from a large electronic medical record ("EMR") system on schedules of varying frequency to efficiently refresh data during the operational day. Other embodiments enhance EMR extract data using other computerized data sources and/or computer analysis of the EMR data. Other embodiments provide efficient data delivery for operational intelligence to optimize integrated, team-based health care delivery as well virtual medicine and transitional care. These and other embodiments are further disclosed herein.

14 Claims, 29 Drawing Sheets

(56) References Cited

U.S. PATENT DOCUMENTS

| | | | |
|---|---|---|---|
| 8,050,944 B2 | 11/2011 | Brummel et al. | |
| 8,321,241 B1 | 11/2012 | Mansour et al. | |
| 8,594,936 B1* | 11/2013 | Koval | G01W 1/10 |
| | | | 702/3 |
| 2002/0128036 A1 | 9/2002 | Yach et al. | |
| 2003/0074222 A1 | 4/2003 | Rosow et al. | |
| 2003/0120527 A1* | 6/2003 | Palomo | G06Q 10/10 |
| | | | 705/2 |
| 2004/0122717 A1 | 6/2004 | Hancock | |
| 2004/0172299 A1 | 9/2004 | Paul | |
| 2005/0002515 A1 | 1/2005 | Mewhinney et al. | |
| 2005/0147130 A1* | 7/2005 | Hurwitz | G06F 17/30578 |
| | | | 370/503 |
| 2006/0004605 A1* | 1/2006 | Donoghue et al. | 705/2 |
| 2006/0031358 A1 | 2/2006 | Canis | |
| 2006/0122865 A1 | 6/2006 | Preiss et al. | |
| 2006/0282302 A1 | 12/2006 | Hussain | |
| 2006/0293920 A1 | 12/2006 | Stroup et al. | |
| 2007/0156455 A1 | 7/2007 | Tarino et al. | |
| 2007/0226010 A1 | 9/2007 | Larsen | |
| 2008/0086328 A1 | 4/2008 | Hertel et al. | |
| 2008/0126133 A1 | 5/2008 | Park | |
| 2008/0154642 A1 | 6/2008 | Marble et al. | |
| 2008/0248875 A1 | 10/2008 | Beatty | |
| 2008/0262882 A1 | 10/2008 | Farrell | |
| 2009/0024414 A1 | 1/2009 | Mansour et al. | |
| 2009/0125328 A1 | 5/2009 | Nevins | |
| 2009/0138283 A1 | 5/2009 | Brown | |
| 2012/0215560 A1 | 8/2012 | Ofek et al. | |
| 2013/0054260 A1 | 2/2013 | Evans | |

\* cited by examiner

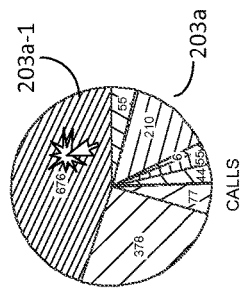

Pt Initiated Calls and Emails Detail
All Modules for All Departments for All Facilities 2000-1

| CONTACT TYPE | STATUS | PCP | MRN | CONTACT TIME | | DEPARTMENT | FACILITY | MODULE |
|---|---|---|---|---|---|---|---|---|
| CALLS | OD COMPLETION | NAME A | ****** | M/D/Y | 2:32:02 PM | PEDS | FAC 1 | FAC1 M0 |
| | OD COMPLETION | NAME B | ****** | M/D/Y | 9:35:16 AM | FM | FAC 2 | FAC2 M0 |
| | OD COMPLETION | NAME B | ****** | M/D/Y | 4:27:56 PM | FM | FAC 2 | FAC2 M0 |
| | OD COMPLETION | NAME B | ****** | M/D/Y | 10:53:29 PM | FM | FAC 2 | FAC2 M0 |
| | OD COMPLETION | NAME B | ****** | M/D/Y | 8:32:53 AM | FM | FAC 2 | FAC2 M0 |
| | OD COMPLETION | NAME C | ****** | M/D/Y | 1:33:07 PM | FM | FAC 3 | FAC3 M0 |
| | OD COMPLETION | NAME B | ****** | M/D/Y | 3:02:25 PM | FM | FAC 2 | FAC2 M0 |
| | OD COMPLETION | NAME C | ****** | M/D/Y | 11:29:21 AM | FM | FAC 3 | FAC3 M0 |
| | OD COMPLETION | NAME B | ****** | M/D/Y | 3:00:24 PM | FM | FAC 2 | FAC2 M0 |
| | OD COMPLETION | NAME B | ****** | M/D/Y | 11:06:13 AM | FM | FAC 2 | FAC2 M0 |
| | OD COMPLETION | NAME D | ****** | M/D/Y | 8:12:03 AM | IM | FAC 4 | FAC4 M0 |
| | OD COMPLETION | NAME D | ****** | M/D/Y | 8:51:52 AM | IM | FAC 4 | FAC4 M0 |
| | OD COMPLETION | NAME C | ****** | M/D/Y | 10:15:43 AM | FM | FAC 4 | FAC4 M0 |
| | OD COMPLETION | NAME E | ****** | M/D/Y | 12:39:28 PM | FM | FAC 5 | FAC5 M0 |
| | OD COMPLETION | NAME D | ****** | M/D/Y | 5:43:40 PM | FM | FAC 4 | FAC4 M0 |
| | OD COMPLETION | NAME D | ****** | M/D/Y | 4:02:51 PM | FM | FAC 4 | FAC4 M0 |

| | | 251 SCHEDULE | 252 CLINICAL QUALITY SERVICE (OFFICE VISITS) | | | | | | | | | | | 253 CLINICAL SUPPORT | | |
|---|---|---|---|---|---|---|---|---|---|---|---|---|---|---|---|---|
| | MA/LPN | VISITS | ALLERGY REVD | MED REVD | BP PTS | BP 1ST | BP 1ST ABN | BP 2ND | TOBACCO REVD | RESP | WT | HT | TEMP | CALL TOUCHES | EMAIL TOUCHES | SENT LETTERS |
| SUMMARY | | 1,314 | 89% | 71% | 1,211 | 97% | 237 | 93% | 84% | 63% | 1,238 | 422 | 1,135 | 1,877 | 815 | 18 |
| NAME MM | | | | | | | | | | | | | | 6 | 15 | |
| NAME PP | | | | | | | | | | | | | | 1 | 12 | |
| NAME QQ | | | | | | | | | | | | | | 1 | 17 | |
| NAME RR | | 3 | 100% | 0% | 3 | 100% | | 100% | 100% | 0% | 3 | | 3 | | | |
| NAME SS | | 7 | 100% | 57% | 6 | 100% | 3 | 100% | 100% | 0% | 7 | | 1 | | 2 | |
| NAME TT | | | | | | | | | | | | | | 4 | 32 | |
| NAME UU | | | | | | | | | | | | | | 16 | | |
| NAME VV | | | | | | | | | | | | | | 1 | | |
| NAME WW | | | | | | | | | | | | | | 19 | 1 | |
| NAME XX | | 3 | 67% | 0% | 3 | 100% | 1 | 100% | 100% | 100% | 3 | 1 | 3 | 3 | | |
| NAME YY | | 6 | 100% | 100% | 6 | 100% | | 100% | 83% | 0% | 6 | 1 | 6 | 6 | | |
| NAME ZZ | | | | | | | | | | | | | | 9 | 14 | |
| NAME AAA | | | | | | | | | | | | | | 6 | 26 | |
| NAME BBB | | | | | | | | | | | | | | 10 | | |
| NAME CCC | | | | | | | | | | | | | | 13 | | |
| NAME DDD | | | | | | | | | | | | | | 8 | | |
| NAME EEE | | 2 | 100% | 100% | 2 | 100% | | | 50% | 100% | 2 | | 2 | 5 | 1 | |
| NAME FFF | | | | | | | | | | | | | | 17 | | |
| NAME GGG | | | | | | | | | | | | | | 3 | 10 | |
| NAME HHH | | | | | | | | | | | | | | 16 | | |
| NAME III | | | | | | | | | | | | | | 2 | | |
| NAME JJJ | | | | | | | | | | | | | | 10 | | |
| NAME KKK | | | | | | | | | | | | | | 8 | 1 | |

2600

291 Incoming Referrals (last 2 weeks)

| Referral Type | 8-14 days | 0-7 days |
|---|---|---|
| TYPE 1 | 11 | 12 |
| TYPE 2 | 6 | 19 |
| TYPE 3 | 6 | 8 |
| TYPE 4 | 23 | 22 |
| TYPE 5 | 1 | 2 |
| TYPE 6 | 8 | 9 |
| TYPE 7 | 28 | 31 |
| TYPE 8 | 5 | 4 |
| TYPE 9 | 14 | 18 |
| TYPE 10 | 6 | 8 |
| TYPE 11 | 12 | 4 |
| TYPE 12 | 22 | 25 |
| TYPE 13 | 45 | 47 |
| TYPE 14 | 29 | 28 |
| TYPE 15 | 0 | 0 |
| TYPE 16 | 0 | 2 |
| TYPE 17 | 0 | 0 |
| TYPE 18 | 0 | 0 |
| TYPE 19 | 0 | 0 |

292 Referrals Within Last 12 Weeks

| Referral Type | Appt'd <=2 days | Appt'd <=9 days | Compl'd/appt'd | Unappt'd <=9 days | Unappt'd >= 9 days | Denied/unaptble | External |
|---|---|---|---|---|---|---|---|
| TYPE 1 | 1 | 3 | 46 | 5 | 24 | 0 | |
| TYPE 2 | 0 | 1 | 66 | 18 | 27 | 0 | |
| TYPE 3 | 0 | 1 | 20 | 9 | 10 | 0 | |
| TYPE 4 | 1 | 6 | 116 | 19 | 45 | 0 | |
| TYPE 5 | 0 | 3 | 11 | 1 | 7 | 0 | |
| TYPE 6 | 3 | 2 | 37 | 10 | 24 | 0 | |
| TYPE 7 | 3 | 4 | 101 | 28 | 44 | 0 | |
| TYPE 8 | 0 | 3 | 15 | 3 | 8 | 0 | |
| TYPE 9 | 2 | 8 | 69 | 9 | 32 | 0 | |
| TYPE 10 | 0 | 3 | 31 | 11 | 17 | 0 | |
| TYPE 11 | 0 | 0 | 124 | 16 | 44 | 0 | |
| TYPE 12 | 0 | 11 | 121 | 19 | 32 | 0 | |
| TYPE 13 | 1 | 27 | 256 | 29 | 26 | 0 | |
| TYPE 14 | 1 | 11 | 147 | 31 | 33 | 0 | |
| TYPE 15 | 0 | 0 | 0 | 0 | 0 | 0 | 2 |
| TYPE 16 | 0 | 2 | 8 | 1 | 2 | 0 | 7 |
| TYPE 17 | 0 | 0 | 0 | 0 | 0 | 0 | 23 |
| TYPE 18 | 0 | 0 | 0 | 0 | 0 | 0 | 134 |
| TYPE 19 | 0 | 0 | 0 | 0 | 0 | 0 | 188 |

293 Unappointed > 9 Days Within Last 12 weeks

| Referral Type | MRN | Auth Reason | Days from Ref Date | Cancelled |
|---|---|---|---|---|
| TYPE 1 | ****** | Apprv – New (sched) | 22 | |
| TYPE 1 | ******* | Apprv – New (sched) | 65 | |
| TYPE 2 | ****** | Apprv – New (sched) | 15 | |
| TYPE 2 | ****** | Apprv – New (sched) | 18 | |
| TYPE 2 | ****** | Apprv – New (sched) | 21 | |
| TYPE 2 | ******* | Apprv – New (sched) | 22 | |
| TYPE 2 | ******* | Apprv – New (sched) | 23 | |
| TYPE 2 | ******* | Apprv – New (sched) | 25 | |
| TYPE 2 | ******* | Apprv – New (sched) | 32 | |
| TYPE 2 | ******* | Apprv – New (sched) | 36 | |

294 Time To First SC Call Back (Last 2 Weeks Referrals)

| Referral Type | <6 Hrs | 6-12 Hrs | 12-24 Hrs | 1-2 Days | 3-7 Days | >=7 Days |
|---|---|---|---|---|---|---|
| TYPE 2 | 0 | 0 | 1 | 0 | 1 | 1 |
| TYPE 3 | 0 | 0 | 0 | 0 | 1 | 0 |
| TYPE 16 | 0 | 0 | 1 | 1 | 0 | 1 |
| TYPE 4 | 4 | 0 | 1 | 4 | 2 | 0 |
| TYPE 5 | 0 | 0 | 1 | 1 | 0 | 1 |
| TYPE 6 | 0 | 0 | 1 | 0 | 1 | 0 |
| TYPE 8 | 0 | 1 | 1 | 1 | 2 | 1 |
| TYPE 9 | 4 | 1 | 5 | 0 | 3 | 0 |
| TYPE 10 | 5 | 0 | 1 | 2 | 6 | 0 |
| TYPE 12 | 6 | 1 | 5 | 2 | 7 | 0 |

FIG. 27

COMPUTER SYSTEM AND METHOD FOR DELIVERING OPERATIONAL INTELLIGENCE FOR AMBULATORY TEAM BASED CARE AND VIRTUAL MEDICINE

CROSS REFERENCE TO RELATED APPLICATIONS

The present application is a continuation of co-pending U.S. application Ser. No. 13/451,536 filed on Apr. 19, 2012.

BACKGROUND

Traditional electronic medical record information ("EMR") systems are optimized for storing historical and current records of individual patients or members. Such systems are transaction oriented and patient centered. The data that these systems capture can be mined to provide intelligence that drives improvements in quality of care for individuals and populations, but the readily accessible information from these systems is generally limited to information on individual physicians who treat patients. Moreover, the time required to pull data from large EMR systems to generate operational intelligence across an enterprise is substantial, limiting its utility for supporting ongoing daily decision making. Direct interface with the native EMR database (which is often a non-relational database) is not practical for advanced analytic purposes, especially for a moderate to large size health care delivery enterprise. For example, in an integrated health care delivery enterprise serving 500,000 active members, the associated EMR system or systems might store on the order of several terabytes of data. Therefore, existing data warehousing systems that import from such large systems for comprehensive process analysis have generally been limited to refreshing data weekly or daily.

Embodiments of the present invention arise in this context.

SUMMARY

Health care delivery is changing in several ways. The operational pace and consequences of inefficiency and suboptimal service and quality have greatly increased. Across settings, team-based care is gaining prominence. Along with Physicians, other health care staff—including associated clinicians, registered nurses ("RNs"), licensed practical nurses ("LPNs"), and medical assistants ("MAs")—play key roles in providing efficient care. Virtual care, including interactions by telephone call and secure email, plays an increasing role in efficient and convenient care delivery. Well-coordinated care between providers is increasingly important to safe and effective care, particularly during transitions between settings.

Improving efficiency, quality, and service in a medium or large integrated health care enterprise requires provider-side data at varying levels of aggregation: individuals, health care teams, departments, specialties, and/or facilities. Process-centered data is also required.

An increasing need exists for operational intelligence derived from reorganized and enhanced information provided by existing electronic medical record ("EMR") systems and integration with other enterprise data sources. Furthermore, in view of the above health care trends, the integrated health care delivery enterprise can benefit from operational intelligence to track information that frequently changes throughout the day. Providing such intelligence requires frequent extracts of time sensitive data from a large EMR system (which is typically non-relational, e.g., hierarchical) so that the data can be mined with advanced analytic techniques. However, this has traditionally not been practical given the size and nature of the EMR systems serving integrated health care enterprises today.

One embodiment of the present invention provides near real time operational intelligence supporting daily ongoing management decisions in the context of integrated and team-based delivery of care. In a particular embodiment, care delivery data is displayable by facility and department (e.g., specialty). In another embodiment, care delivery data is also displayable by module (e.g., a smaller team within a facility or department team). One embodiment of the invention supplements EMR system data to identify provider relationships including facility, department, and/or module. In one alternative embodiment, the supplemental data is received from another data system. In another alternative embodiment, the supplemental data is derived using data from the EMR system. In one embodiment, dyads are identified including a physician and a medical support person such as a Licensed Practical Nurse ("LPN") or a medical assistant ("MA").

In another embodiment, support care data is displayable for individual support care providers. In a particular embodiment, support care data includes visit tasks such as blood pressure, allergy checks, current medication checks, tobacco checks, weight, and temperature and an individual medical assistant level (e.g., LPN or MA). In a particular embodiment, such data is refreshed on a near real-time basis.

One embodiment provides support for real-time or near real-time operational decisions related to transitional medical care. In a particular embodiment, patient contacts related to inpatient admissions and discharges are tracked and displayable as well as data related to discharge follow-up tasks.

One embodiment provides near real time support for operational decisions related to virtual medicine. In a particular embodiment, contacts related to calls and emails are tracked by facility and department. In another embodiment, such contacts are also tracked by module.

One embodiment of the present invention provides a system and method for efficiently extracting care delivery data from a large transaction-oriented EMR data system at varied intervals throughout the day. In one embodiment, different data is extracted at different frequencies from the EMR system to refresh an operational data store on a near real time basis. In a particular embodiment, first selected data is extracted daily, second selected data is extracted hourly, and third selected data is extracted intra-hourly.

These and other embodiments are described more fully below. For purposes of illustration only, several aspects of particular embodiments of the invention are described by reference to the following figures.

BRIEF DESCRIPTION OF THE DRAWINGS

FIG. 20 illustrates an exemplary user interface for a detailed report regarding patient initiated calls and emails accessible from the overview tab of FIG. 19.

FIG. 23 illustrates an exemplary calls/emails tab of a user interface generated by the embodiment of FIG. 1.

FIG. 24 illustrates an exemplary support tab of a user interface generated by the embodiment of FIG. 1.

FIG. 27 illustrates an exemplary referrals tab for a specialty care user interface generated by the embodiment of FIG. 1.

DETAILED DESCRIPTION

The following description is presented to enable any person skilled in the art to make and use the invention, and is provided in the context of particular applications and their requirements. Various modifications to the exemplary embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles and features disclosed herein.

Figure 1:
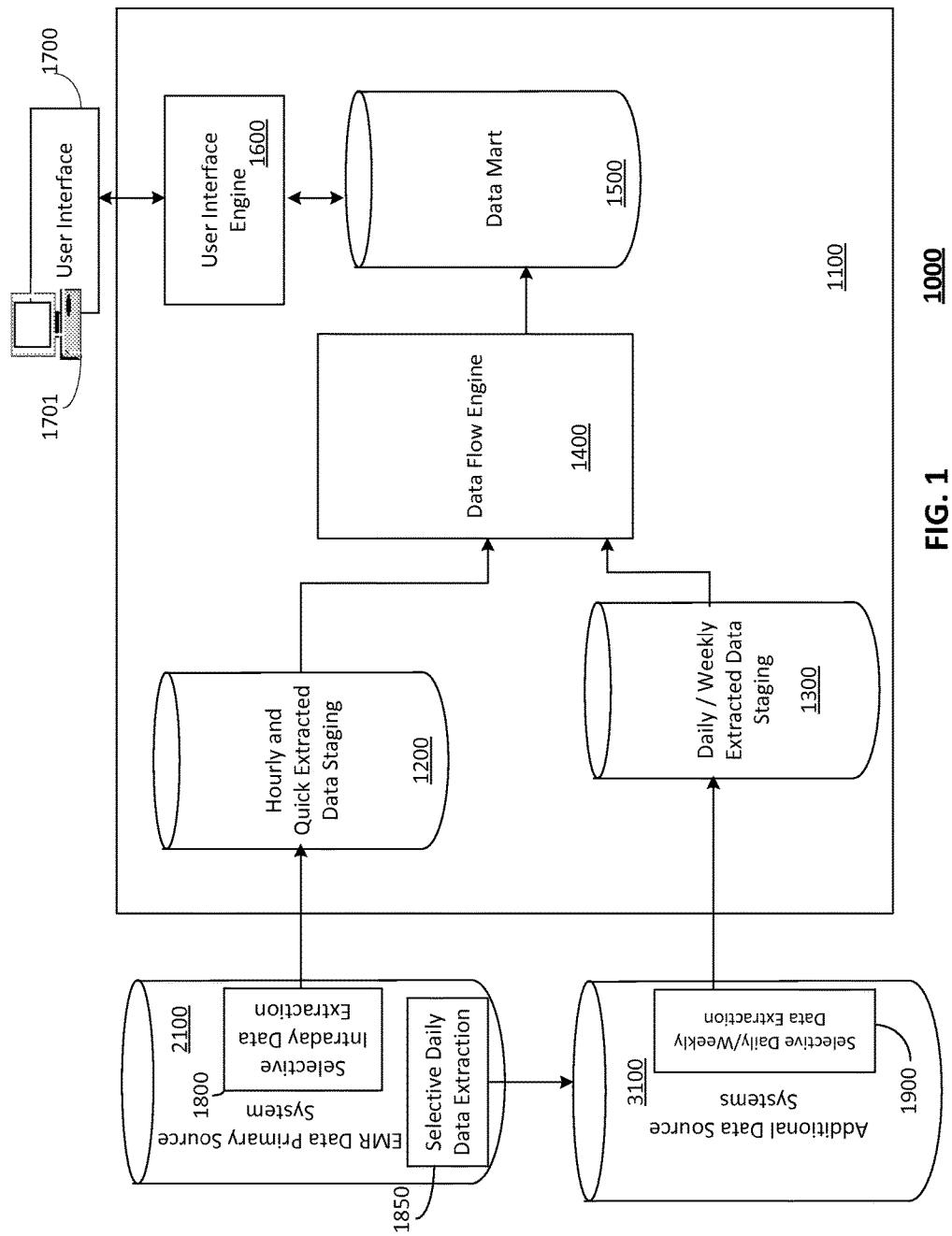
FIG. 1 illustrates a health care optimization system in accordance with an embodiment of the present invention.

FIG. 1 illustrates medical care optimization system 1000 including operational data engine system 1100 and data source systems 2100 and 3100. System 1000 is in accordance with an embodiment of the present invention; however, it should be understood that some parts of system 1000 provide context for embodiments of the invention and are not necessarily themselves part of the illustrated invention embodiment.

Operational data engine 1100 includes Hourly and Quick Extracted Data Staging Server 1200, Daily/Weekly Extracted Data Staging Server 1300, Data Flow Engine 1400, Data Mart 1500 and User Interface Engine 1600.

User Interface Engine 1600 communicates with user interface 1700 of an end user device such as end user device 1701. As will be appreciated by those skilled in the art, end user device 1701 may comprise any device capable of interacting with and communicating data to an end user. In particular context, it may be a personal computer, mobile phone, touchpad, or other such device. Such devices have known user input capability including the ability to display data through a screen and/or speaker and/or tactile output and the ability receive user input command through a mouse, touchpad, touch stick, key board, microphone, optical or other free space sensor, touchscreen, pressure sensor, and/or other such input elements. It will be understood that an end user device such as device 1701 may communicate with system 1100 through any one of various types of connections including, for example direct wired or wireless connections or through various network connections such as, for example, a local area network, the Internet, and/or a wireless network connection.

In particular embodiments, the illustrated components of system 1100 may be implemented using one computer or more than one computer. Moreover, while the components are illustrated as distinct from each other and are implemented using multiple computers, in alternative embodiments, the illustrated components may be implemented as single components with multiple functions. For example, data staging servers 1200 and 1300 may be implemented on separate data server computers or may be implemented as part of the same data server and may be implemented on the same or different computer as Data Flow Engine 1400, Data Mart 1500 and User Interface Engine 1600. In this case, each of staging server 1200 and 1300 comprise logic and storage for storing extracted data (which may be received in various formats such as, for example, flat files) in data tables for use by Data Flow Engine 1400. Data Mart 1500 comprises data stored in tables for use by user interface engine 1600. Various process logic routines of the illustrated components may be implemented using executable computer code stored on system 1100 in a computer readable medium, such as, for example, a computer memory and/or persistent data storage device of or coupled to system 1100.

Source system 2100 is an electronic medical record ("EMR") system that stores patient medical records. In this example, source system 2100 includes a shadow computer server that shadows a live transaction-oriented EMR system. However, in alternative embodiments, source system may be a live transaction-oriented EMR system itself rather than a shadow server.

Selective intraday data extraction engine 1800 is configured to execute data extractions from EMR system 2100 and send them to Hourly and Quick Data Staging server 1200. Data in EMR system 2100 is stored on one or more non-volatile computer storage devices in system 2100 such as, for example, a magnetic disc. Data extraction engine 1800 (as well as Selective Daily Data Extraction module 1850) may be implemented using executable computer code stored on system 2100 in a computer readable medium, such as, for example, a computer memory and/or persistent data storage device of system 2100. It will be appreciated by those skilled in the art that in an alternative embodiments, all or a portion of a data extraction engine such as engine 1800 may reside on another computer system such as, for example, one of the one or more computers of system 1100.

Additional Data Source Systems 3100 comprise one or more additional computer servers configured to receive, store, and export data. In this particular example, some data in data source systems 3100 includes a portion of data stored in EMR system 2100 that is exported daily from system 2100 to system 3100 by Selective Daily Data Extraction module 1850. Another portion of data in data source systems 3100 is obtained from other systems. In various embodiments, examples of such other systems include payroll systems, medical clinic administrative systems, or various enterprise specific data systems. In one example, provider module data is not obtained directly or indirectly from EMR system 2100 but is instead obtained from enterprise specific data systems that are part of additional data source systems 3100. Selective Daily/Weekly Data extraction module 1900 exports selected data to Daily/Weekly Extracted Data Staging server 1300.

Data flow engine 1400 operates on data held by Hourly and Quick Extracted Data Staging server 1200 and Daily/Weekly Extracted Data Staging server 1300 and uses that data and the results of operations on that data to populate Data Mart 1500. Data Mart 1500 includes data stored in table structures usable by User Interface Engine 1600 to provide data displays via user interface 1700.

It should be emphasized that the separation of various components in the illustrated example is, in some respects, simply to facilitate easier of explanation of the operations of a system such as system 1000. For example, although the embodiment of FIG. 1 illustrates presents data staging servers 1200 and 1300 as distinct from Data Flow Engine 1400, in a particular embodiment, these servers may simply represent sets of data tables maintained by logic that is part of Data Flow Engine 1400. Moreover, in some embodiments, at least certain extracted data is used directly by data flow engine 1400 without being stored in staging tables.

Figure 2:
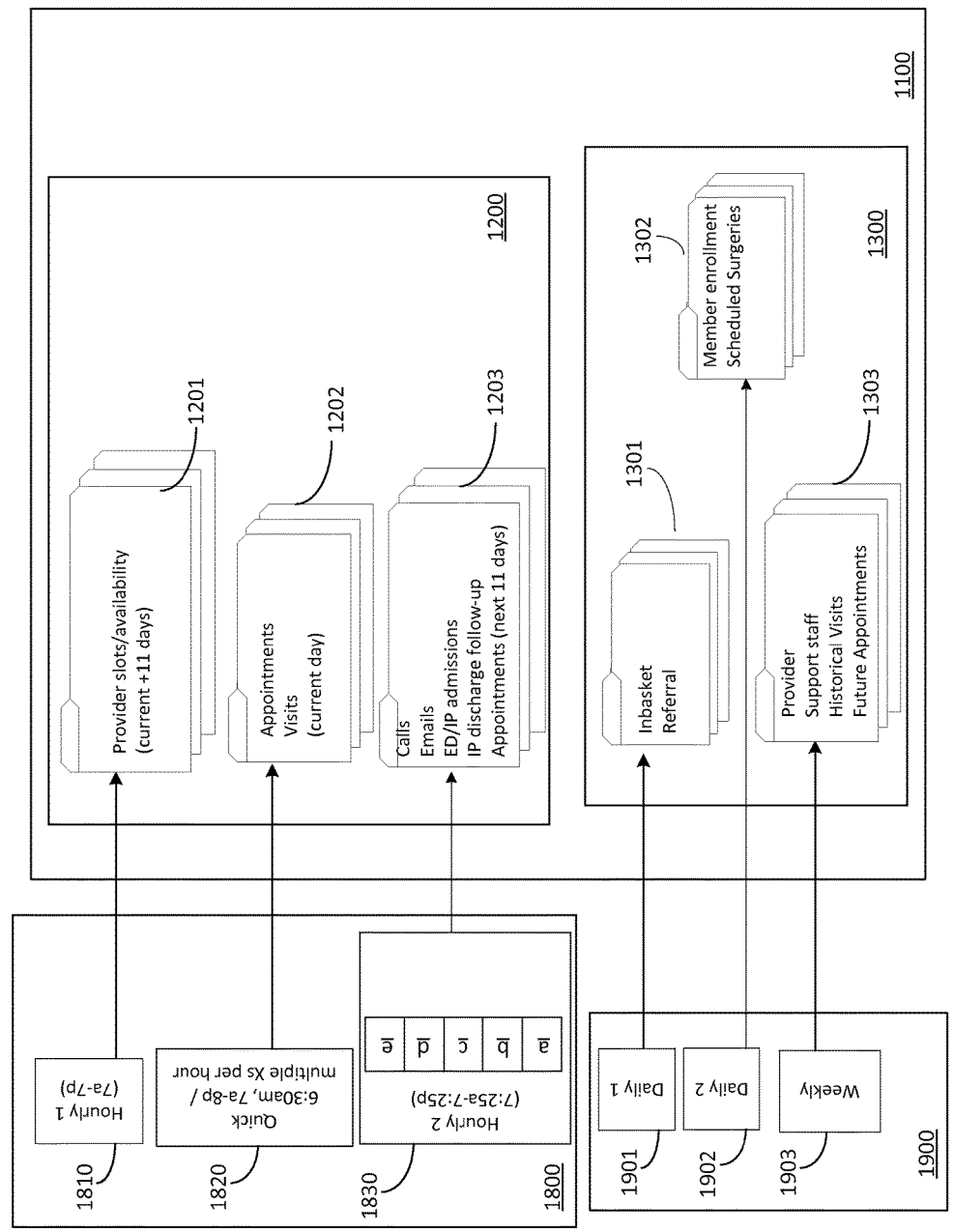
FIG. 2 illustrates further details of data extract components of the embodiment of FIG. 1.

FIG. 2 illustrates further details of data extract components of the embodiment of FIG. 1. In particular, Selective Intraday Extraction Engine 1800 includes "Hourly 1" extraction module 1810, "Quick" extraction module 1820, and "Hourly 2" extraction module 1830. In this example, Hourly 1 extraction module is configured to run data extractions once per hour between 7 am and 7 pm. Quick extraction module 1820 is configured to run data extractions multiple times per hour between 7 am and 8 pm. In one embodiment, Quick extraction module 1820 runs data extractions every 15 minutes. In another embodiment, Quick extraction module runs data extractions every 10 minutes. In another embodiment, Quick extraction module 1820 runs data extractions every 5 minutes. Hourly 2 extraction module 1830 is configured to run data extractions every hour between 7:25 am and 7:25 pm.

Hourly 1 extraction module 1810 extracts data regarding provider availability (e.g., when providers are available to see patients) for the next 11 days. In the illustrated example, data is sent via flat files to data staging 1200 portion of system 1100 where it is then organized and stored in data staging tables 1201.

Quick extraction module 1820 extracts current day data regarding appointments (e.g., what appointments are scheduled for the current day) and visits (e.g., various data relating to a particular patient visit). In the illustrated example, data is sent via flat files to data staging 1200 portion of system 1100 where it is organized and stored in data staging tables 1202.

Hourly 2 extraction module 1830 extracts current day data regarding calls and emails; inpatient ("IP") and emergency department ("ED") admissions; IP discharge and related follow-up tracking; and upcoming patient encounters (e.g., selected visit, immunization, or other appointments) for the next several days. (In an alternative embodiment, ED/IP admissions and IP discharge and follow-up data is extracted by a quick extraction module such as module 1820). In the illustrated example, data is sent via flat files to data staging 1200 portion of system 1100 where it is organized and stored in data staging tables 1203. Hourly 2 extraction module 1830 includes sub-modules 1830a, 1830b, 1830c, 1830d, 1830e, and 1830s which operate as further described in the context FIGS. 5-10 (sub-module 1830s is shown in FIG. 10 but not separately shown here in FIG. 2).

Daily extraction module 1901 sends in-basket data (e.g., charting tasks, prescription orders, and others) and referral data to data staging portion 1300 of system 1100 where it is stored in data staging tables 1301. Daily extraction module 1902 sends member enrollment data to data staging 1300 portion of system 1100 where it is organized and stored in data staging tables 1302. In the illustrated embodiment, weekly extraction module 1903 sends selected provider data including data regarding physicians, register nurses ("RNs"), and associated clinicians ("ACs") (e.g., physician assistants, nurse practitioners) as well as data regarding medical assistants ("MAs"), and licensed practical nurses ("LPNs") to data staging 1300 portion of system 1100 where it is organized and stored in data staging tables 1303. Weekly extraction module 1903 also sends historical visits data (in this example, for the past 30 days) and future appointments data (in this example, for the next 30 days) to data staging 1303.

Figure 3:
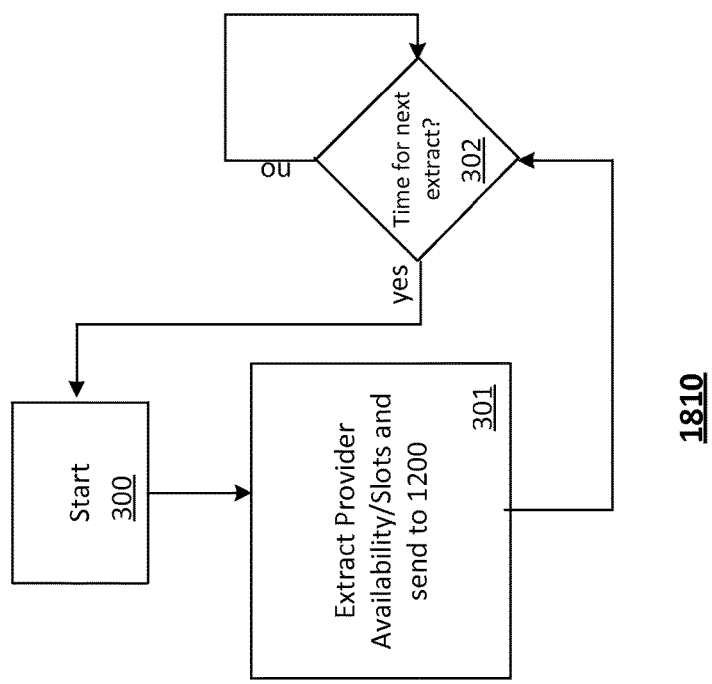
FIG. 3 illustrates process steps carried out by a portion of the data extract components illustrated in FIG. 2.

FIG. 3 illustrates process steps carried out by Hourly 1 extraction module 1810 of FIG. 2. The process begins at step 300. Step 301 extracts data for provider schedules (provider availability/slots) and sends it to data staging 1200 of system 1100. Step 302 determines if it is time for the next Hourly 1 extract and, if so, the process starts again at step 300.

Figure 4:
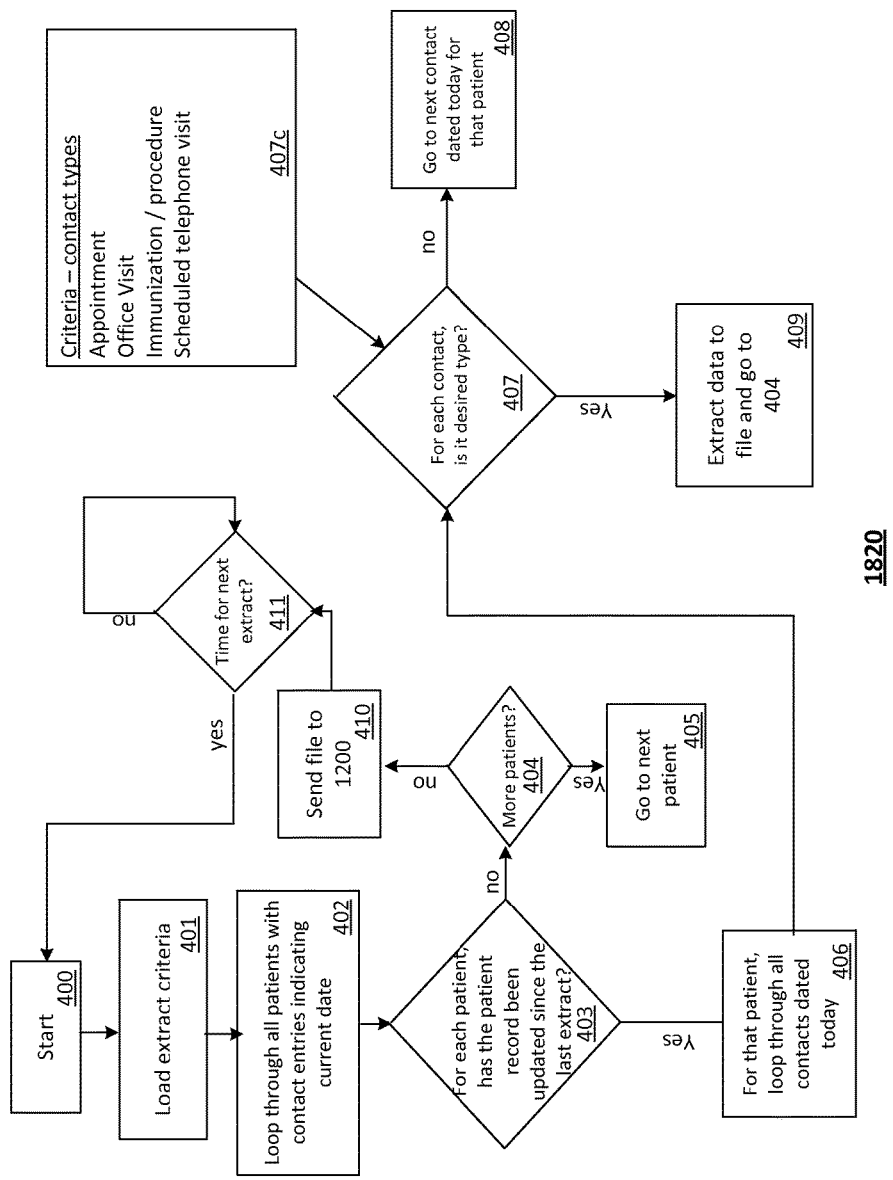
FIG. 4 illustrates additional process steps carried out by a portion of the data extract components illustrated in FIG. 2.

FIG. 4 illustrates process steps carried out by Quick extraction module 1820 of FIG. 2. The process begins at step

400. Step 401 loads extraction criteria. These criteria define which fields from a particular record are extracted as further explained below. Step 402 begins looping through all patients with a contact entry having the current day's date. For each patient, step 403 determines whether the patient record has been updated since the last extract. In one embodiment, this is accomplished by comparing a time stamp of the most recent patient record update to a time stamp of the prior extract. If the result of step 403 is no, then step 404 determines whether there are more patients for consideration by step 403. If yes, then step 405 goes to the next patient. If no, then step 409 determines when it is time for the next Quick extract 1820. If the result of step 403 is yes, then step 406 loops through all contacts dated today for that patient. For each contact, step 407 determines whether it is a contact type to be extracted for this extract using the criteria indicated in table 407*c*. Table 407*c* identifies the contact types for which data should be pulled for this particular extract. If the result of step 407 is no, then step 408 goes to the next contact for that patient. If the result of step 407 is yes, then the data for that contact is extracted at step 408 and the process returns to step 404.

Figure 5:
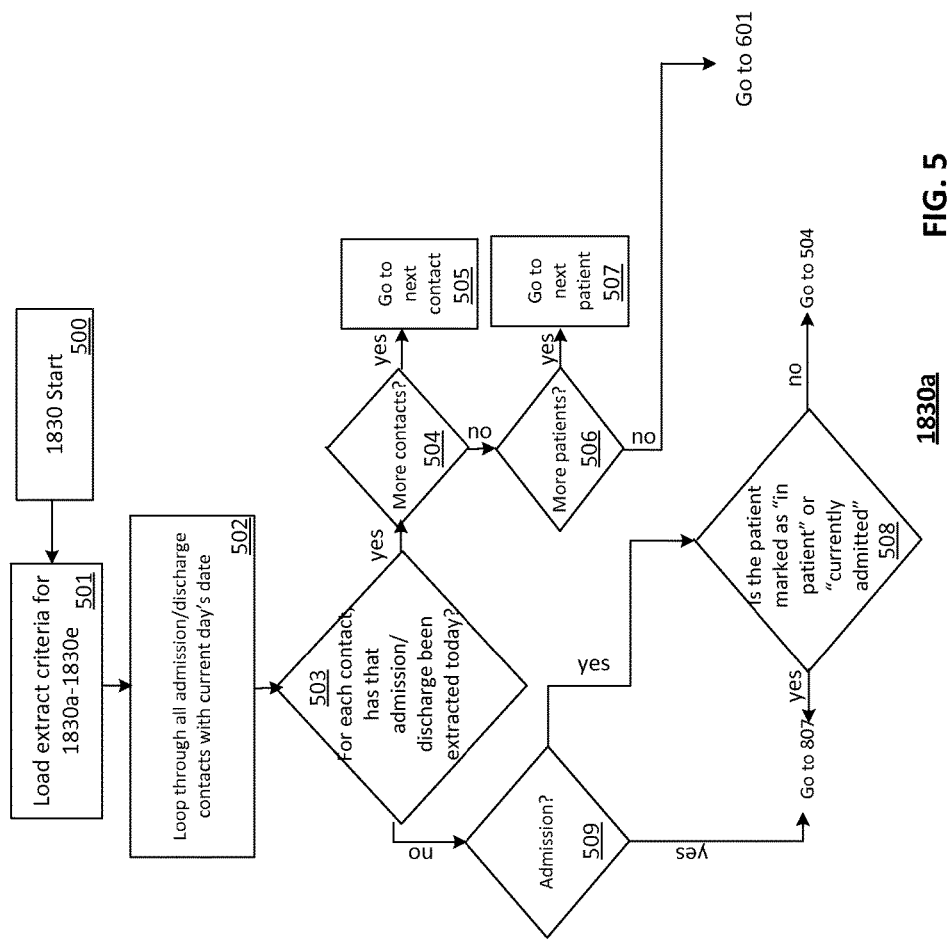
FIG. 5 illustrates additional process steps carried out by a portion of the data extract components illustrated in FIG. 2.

FIG. 5 illustrates process steps carried out by sub-module 1830*a*, which is the initial module of Hourly 2 extraction module 1830 of FIG. 2. The process begins at step 500. Step 501 loads extraction criteria for sub-modules 1830*a*, 1830*b*, 1830*c*, 1830*d*, and 1830*e* of extraction module 1830. These criteria define which fields from a particular record are extracted during execution of a particular sub-module as further explained below. Step 502 begins looping through all admission or discharge contact records with the current day's date.

Step 503 determines whether the discharge/admission has already been extracted today. If yes, step 504 determines whether there are more contacts to be considered for that patient. If the result of step 504 is yes, then step 505 goes to the next contact. If the result of step 504 is no, then step 506 determines whether there are more patients with admission/discharge records for the current day. If the result of step 506 is yes, then step 507 goes to the next patient. If the result of step 506 is no, then the extraction routine moves to step 601 of the process for next sub-module, sub-module 1830*b*.

Figure 8A:
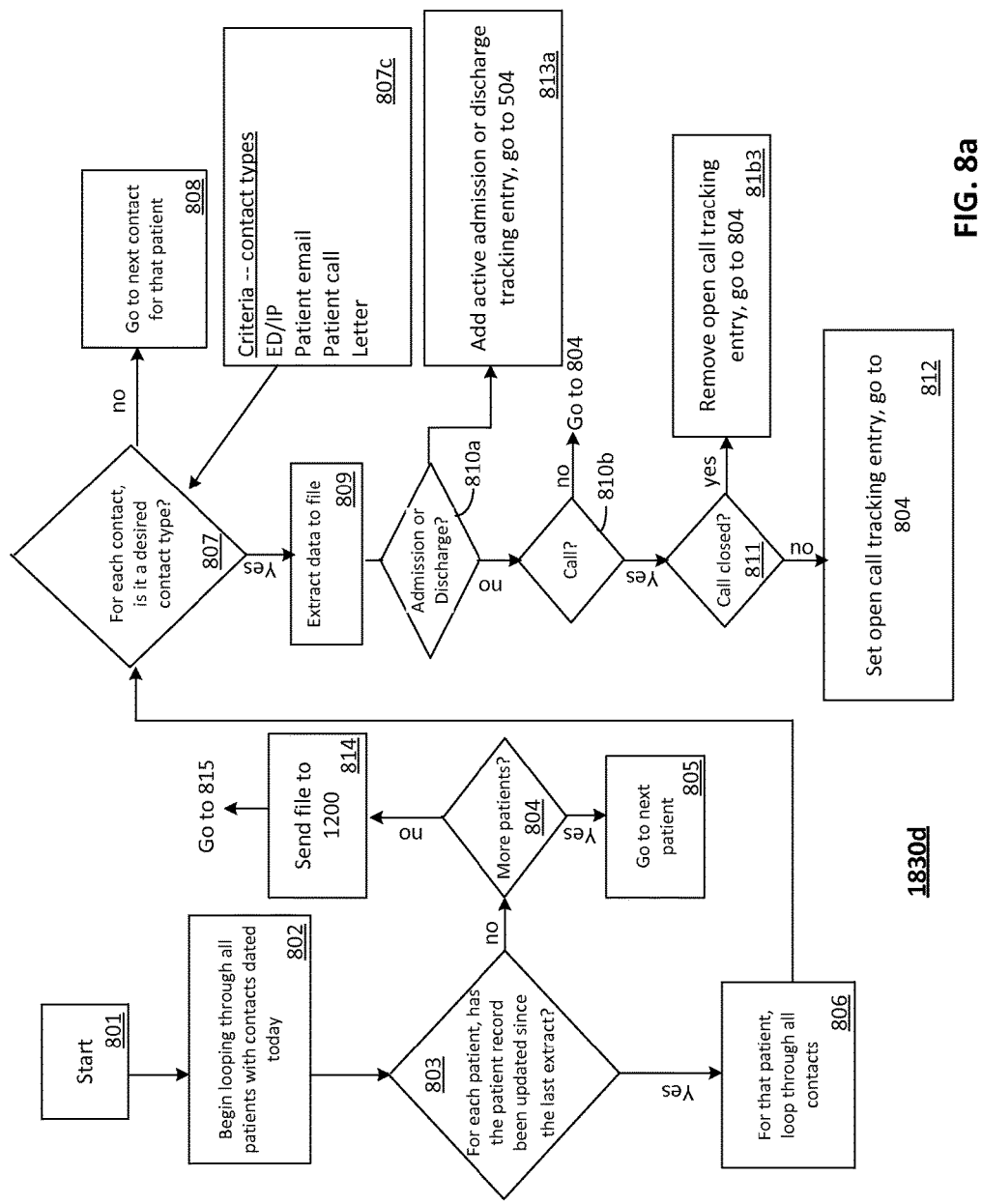
FIG. 8 illustrates additional process steps carried out by a portion of the data extract components illustrated in FIG. 2.

If the result of step 503 is no, then step 509 determines if the contact is an admission. If no, then the routine proceeds to step 807 of sub-module 1830*d* (FIG. 8*a*). If the result of step 509 is yes, then step 508 determines if the patient has been marked in the EMR system as "currently admitted" or "in patient." If no, the process returns to step 504. If yes, then the routine proceeds to step 807 of sub-module 1830*d* (FIG. 8*a*).

Figure 6:
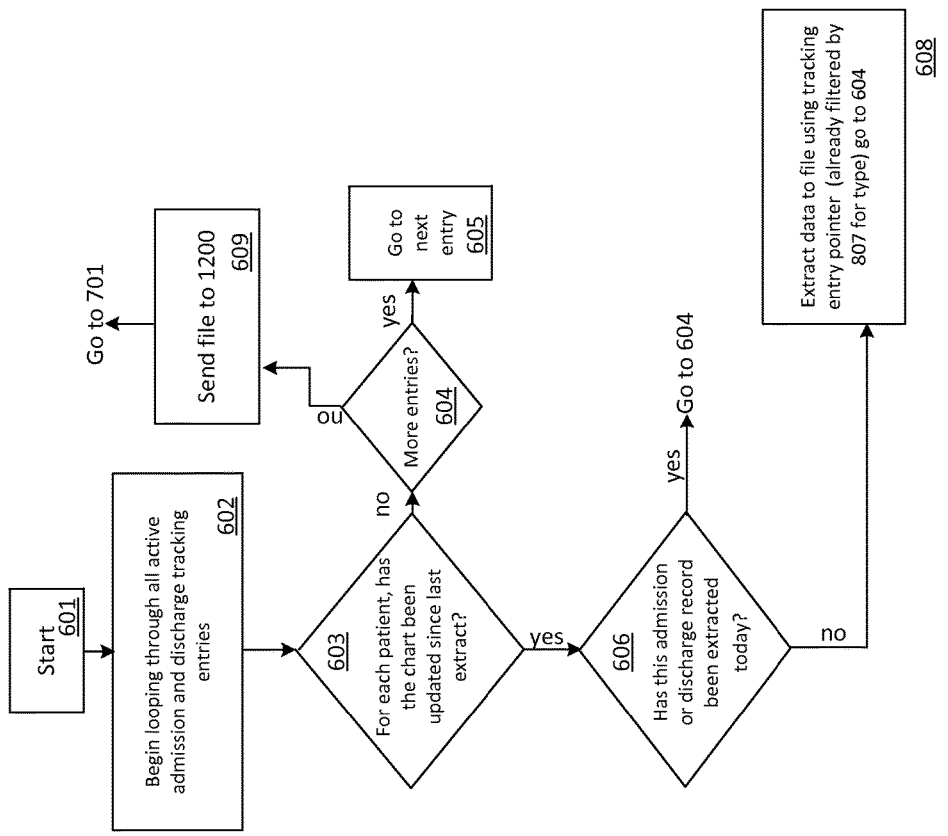
FIG. 6 illustrates additional process steps carried out by a portion of the data extract components illustrated in FIG. 2.

FIG. 6 illustrates process steps carried out by sub-module 1830*b*, which is part of Hourly 2 extraction module 1830 of FIG. 2. The process begins at step 601. Step 602 begins looping through all active admission tracking entries and all discharge tracking entries stored in the temporary file indicated at step 813*a* of sub-module 1830*d* (see FIG. 8). For each patient with an active admission or discharge tracking entry, step 603 determines whether the patient chart has been updated since the last extract. If no, then step 604 determines whether there are more active admission tracking entries or discharge tracking entries. If the result of step 604 is yes, then step 605 goes to the next entry. If the result of step 604 is no, then step 609 sends a file of all data extracted by step 608 (as further described below) to data staging 1200 of system 1100 and the extraction routine moves to step 701 of the process for next sub-module, sub-module 1830*c*.

If the result of step 603 is yes, then step 606 determines whether the associated admission or discharge record has been extracted today. If yes, then the process returns to step 604. If no, then step 608 extracts the data for that contact (the tracking entry includes a pointer to the data, which has already been checked for type—admission or discharge—by step 807 of FIG. 8) to a file for sending by step 609 (as described above) and the process returns to step 604.

Figure 7:
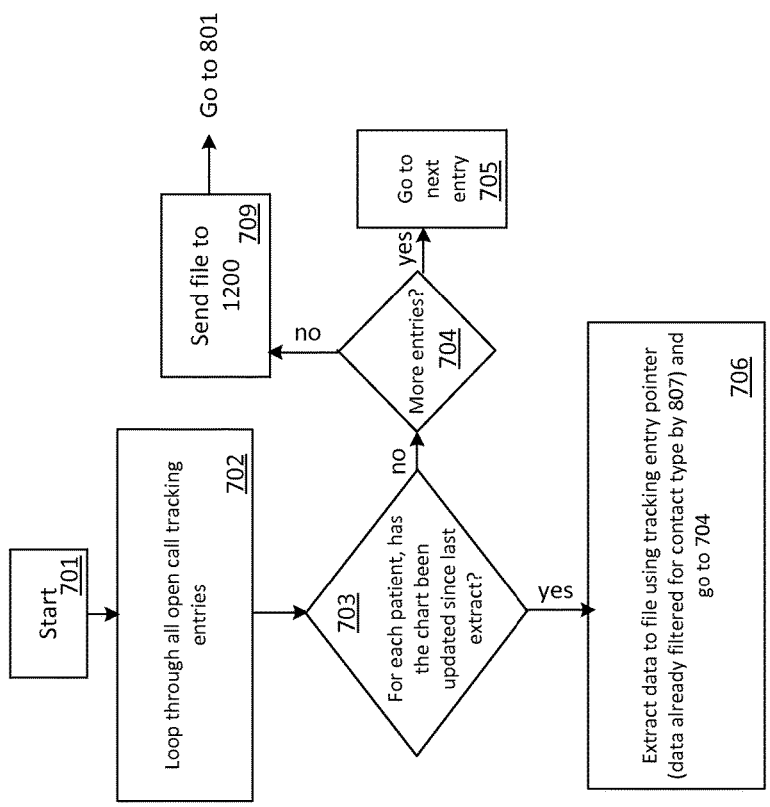
FIG. 7 illustrates additional process steps carried out by a portion of the data extract components illustrated in FIG. 2.

FIG. 7 illustrates process steps carried out by sub-module 1830*c*, which is part of Hourly 2 extraction module 1830 of FIG. 2. The process begins at step 701. Step 702 begins looping through all open call tracking entries. For each patient with an open call tracking entry, step 703 determines whether the patient chart has been updated since the last extract. If no, then step 704 determines whether there are any more open call tracking entries. If the result of step 704 is yes, then step 705 goes to the next entry. If the result of step 704 is no, then step 709 sends a file of all data extracted by step 706 (as further described below) to data staging 1200 of system 1100 and the extraction routine moves to step 801 of the process for next sub-module, sub-module 1830*d*.

If the result of step 703 is yes, then step 706 extracts the data (the tracking entry includes a pointer to the data, which has already been checked for type by step 807 of FIG. 8) to a file for later sending by step 709 (as described above). The process then goes to step 704.

Figure 8B:
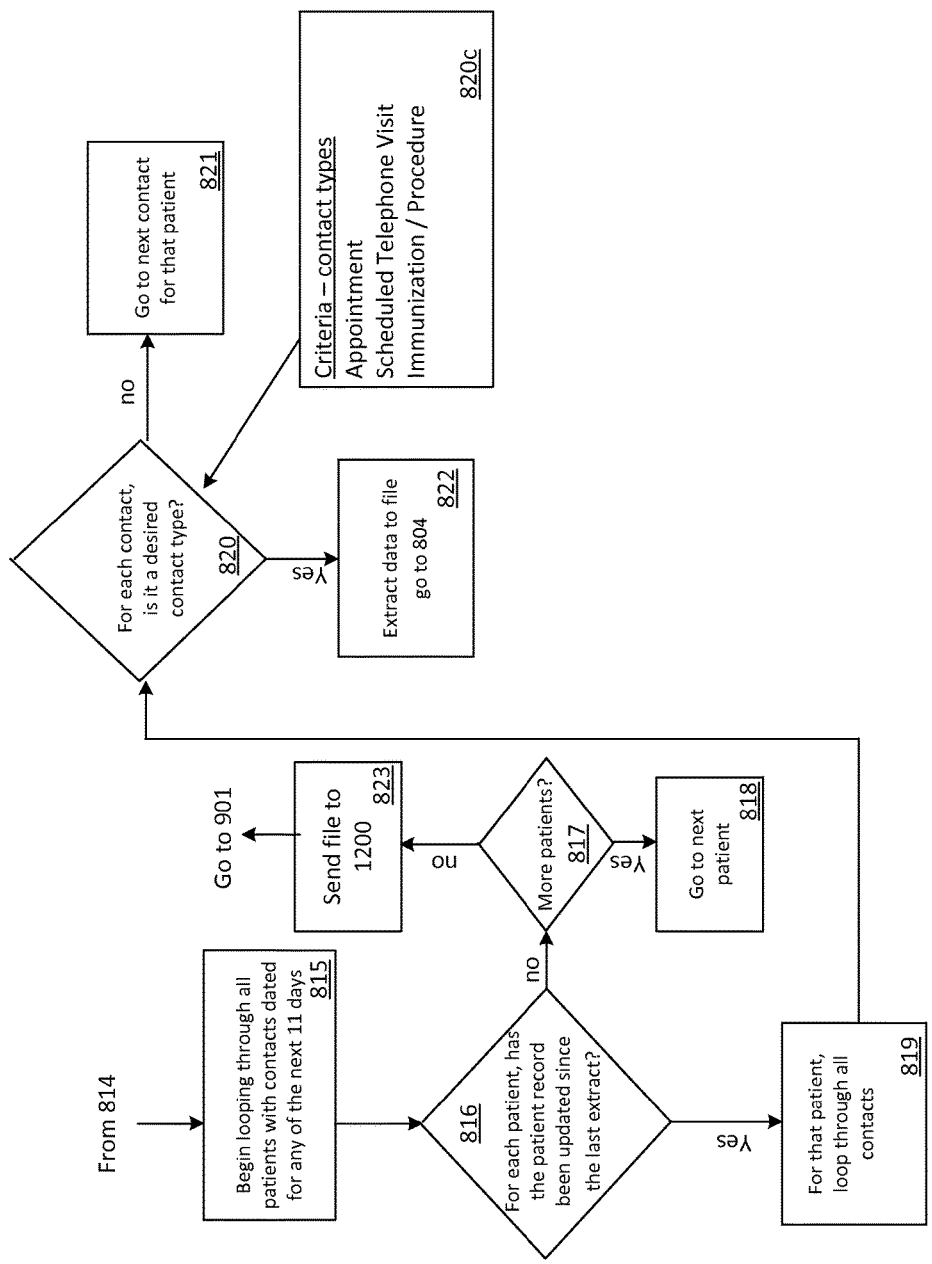

FIGS. 8*a*-8*b* illustrate process steps carried out by sub-module 1830*d*, which is part of Hourly 2 extraction module 1830 of FIG. 2. Referring to FIG. 8*a*, the process begins at step 801. Step 802 begins looping through patients with contacts that have the current day's date. For each patient, step 803 determines whether the patient record has been updated since the last extract. If the result of step 803 is no, then step 804 determines whether there are more patients for consideration by step 803. If yes, then step 805 goes to the next patient. If no, then step 814 sends a file of all data extracted by step 809 (as further described below) to data staging 1200 of system 1100 and the process moves to step 815 (shown in FIG. 8*b*).

If the result of step 803 is yes, then step 806 loops through all contacts dated today for that patient. For each contact, step 807 determines whether it is a contact type to be extracted for this extract using the criteria in table 807*c*. In this example, the desired contact types include hospital encounters, patient emails, telephone encounters, and letters. If the result of step 807 is no, then step 808 goes to the next contact for that patient. If the result of step 807 is yes, then at step 809 the data is extracted to a file for later transmission by step 814 (as described above). Step 810 then determines if the extracted contact was a call. If no, then the process returns to step 804. If yes, then step 811 determines whether the call was closed by looking for a call closed indication in the call record. If no, then step 812 sets an open call tracking entry and the process returns to step 804. If yes, then step 813 removes the open call tracking entry and the process returns to step 804.

Referring to FIG. 8*b*, step 815 begins looping through patient with contacts having a date of any date for the future 11 days. For each patient, step 816 determines whether the patient record has been updated since the last extract. If the result of step 816 is no, then step 817 determines whether there are more patients for consideration by step 816. If yes, then step 818 goes to the next patient. If no, then step 823 sends a file of all data extracted by step 822 (as further described below) to data staging 1200 of system 1100 and the extraction routine moves to step 901 of the next sub-module, sub-module 1830*e* (shown in FIG. 9).

If the result of step 816 is yes, then step 819 loops through all contacts dated in the 11 days after today. For each contact, step 820 determines whether it is a contact type to be extracted for this extract using the criteria in table 820c. In this example, the desired contact types include appointments, immunizations, OB initial office visits and other OB office visits and procedures. If the result of step 820 is no, then step 821 goes to the next contact for that patient. If the result of step 820 is yes, then at step 822 the data is extracted to a file for later transmission by step 823 (as described above).

Figure 9:
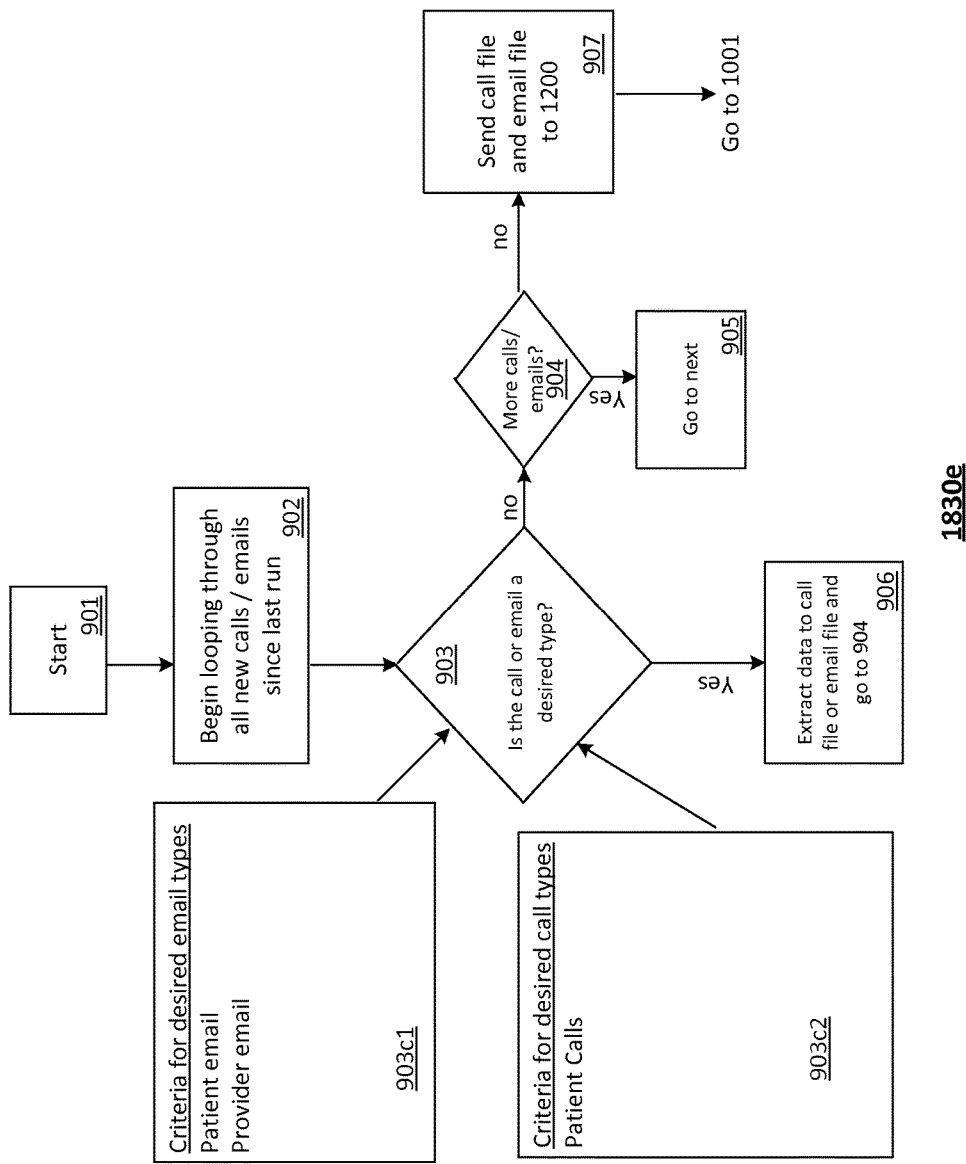
FIG. 9 illustrates additional process steps carried out by a portion of the data extract components illustrated in FIG. 2.
Figure 10:
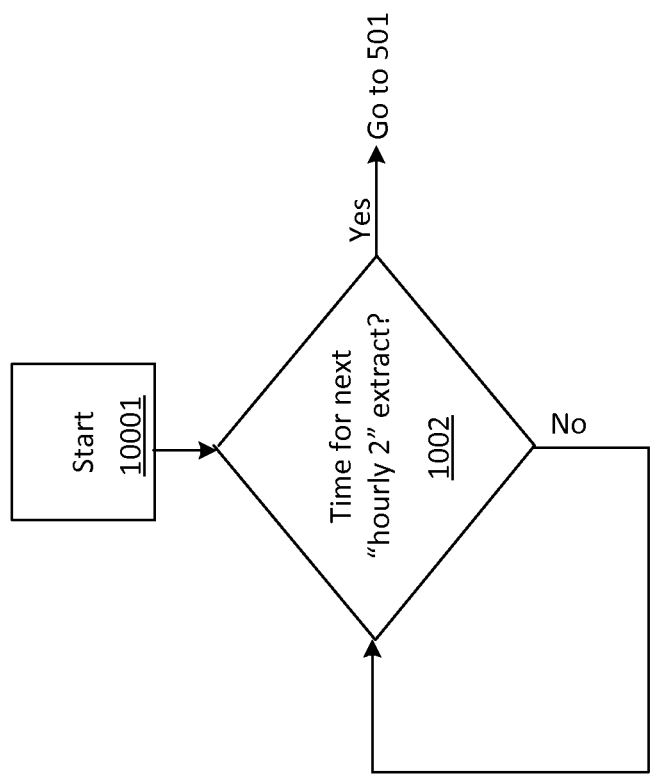
FIG. 10 illustrates additional process steps carried out by a portion of the data extract components illustrated in FIG. 2.

FIG. 9 illustrates process steps carried out by carried out by sub-module 1830e, which is part of Hourly 2 extraction module 1830 of FIG. 2. The process starts at step 901. Step 902 begins looping through all new call and email entries generated since the last extraction. Step 903 determines whether this is a call or email type to be extracted for this extract. For emails, step 903 uses the criteria in table 903c1, which, in this example includes user messages, patient medical advice requests, emails, web contacts, and charts attached to an email. For calls, step 903 uses the criteria in table 903c2 which, in this example, include telephone calls, patient calls, messages to patients, and patient messages. If the result of step 903 is no, then step 904 determines whether there are any more calls or emails generated since the last extract run. If yes, then step 905 goes to the next call or email. If no, then step 907 sends a file of all data extracted by step 906 (as further described below) to data staging 1200 of system 1100 and the extraction routine moves to step 1001 of the next sub-module, sub-module 1830s (shown in FIG. 10). If the result of step 903 is yes, then at step 906 the data is extracted to a file for later transmission by step 907 (as just described) and the process returns to step 904.

FIG. 10 illustrates process steps carried out by carried out by scheduling sub-module 1830s, which is part of Hourly 2 extraction module 1830 of FIG. 2 (though not shown separately in FIG. 2). The process begins at step 1001. Step 1002 determine when it is time for the next "Hourly 2" extract and, when yes, the process returns to step 501 of sub-module 1830a (see FIG. 5).

FIGS. 11-18 illustrate certain exemplary processes carried out by data flow engine 1400 of the embodiment of FIG. 1 and that are used in preparing data for display in user interface views such as those illustrated in FIGS. 19-27. Various data combinations are usable for such purposes.

For example, provider availability/slots data (such as that referenced in block 1201 of FIG. 2) may be used including data for fields such as provider identifier, department, slot begin date, slot length, appointment block/block category, original number of appointments, scheduled number of appointments, as well as appointment number of open appointments.

Contacts data related to current day appointments (such as referred to in block 1202 of FIG. 2) may be used. In one embodiment, an appointment is considered a "visit" once the patient checks in. Appointments data may include data for fields such as appointment type, appointment time, and appointment location/department. In one embodiment, primary care department and location is represented together as one data item. In another embodiment, they may be different data items. Appointment data may also include data for fields such as appointment status (e.g., scheduled, arrived, waiting, exam room, completed), patient identification (e.g. medical record number ("MRN")), and appointment provider identification ("identification" sometimes referenced herein as "ID") i.e., of the provider that the patient is seeing or saw at the appointment. In one embodiment, a provider is a physician or associated clinician. Appointment data may also include data for a field identifying the patient's assigned primary care provider ("PCP"). Appointment data may also include data for fields about clinical tasks performed by medical support staff, for example, by a licensed practical nurse "LPN," or a medical assistant "MA." The clinical tasks data may include data for fields such as first blood pressure, first blood pressure time stamp, first blood pressure recorded by (i.e., who recorded it), allergies reviewed, allergies reviewed by, current meds review, current meds reviewed by, etc. Appointments data may also include data for a field such as the patient's check in time.

Contacts data related to calls and emails ("emails" used herein to refer to certain types of electronic messages) may also be used (such as that referenced in block 1203 of FIG. 2) and may include data for fields such as message ID, parent email, time, message type, person assigned to handle the call or email (e.g., a provider or medical support person), entry logs in the record (which may correspond to distinct "touches" and may include time data, user data, and other data), status (e.g., resolved or open), and patient identification.

Referrals data (such as that referenced in block 1301 of FIG. 2) may be used that includes data for fields such as referring provider, PCP of patient, department of patient's PCP, referring department-facility, referred to department-facility, referral type, referral order date, referral appointment time, referred to specialty, appointment made date, referral note type, referral note date, authorized reason, and patient.

Emergency department ("ED") and inpatient ("IP") admission and IP discharge/discharge follow-up data (such as that referenced in block 1203 of FIG. 2) may be used and include data for fields such as patient, hospital name, admission status, discharge status, admission date, discharge data, and admission reason.

Historical visits data and future appointments data (such as that referenced in block 1303 of FIG. 2) include data for fields similar to that of appointments data referenced above but, in this example, include data for the past 30 days of completed visited and the next 30 days of scheduled appointments.

Provider data (such as that referenced in block 1303 of FIG. 2) may be used that includes data for fields such as provider name, title, ID, user ID, home department/facility, specialty, title, and adjusted panel size. In one embodiment, some or all of the provider data may be included in and/or derivable from the historical visits and future appointments data. In another embodiment, data for some fields may be received separately. In one embodiment, data received separately may be corrected based on analysis of provider related data in the historical visits and future appointments data. Medical support staff data include data for such fields as name, title, ID, user ID, department-facility, and login location. In one embodiment, some of the support staff data may be included in and/or derivable from the historical visits and future appointments data. In another embodiment, data for some or all fields may be received separately. In one embodiment, data received separately may be corrected based on analysis of support staff and provider related data in the historical visits data.

Those skilled in the art will appreciate that the fields referenced above are only examples and represent a small subset of the data variables potentially handled by a system such as the embodiment of FIG. 1.

Figure 11:
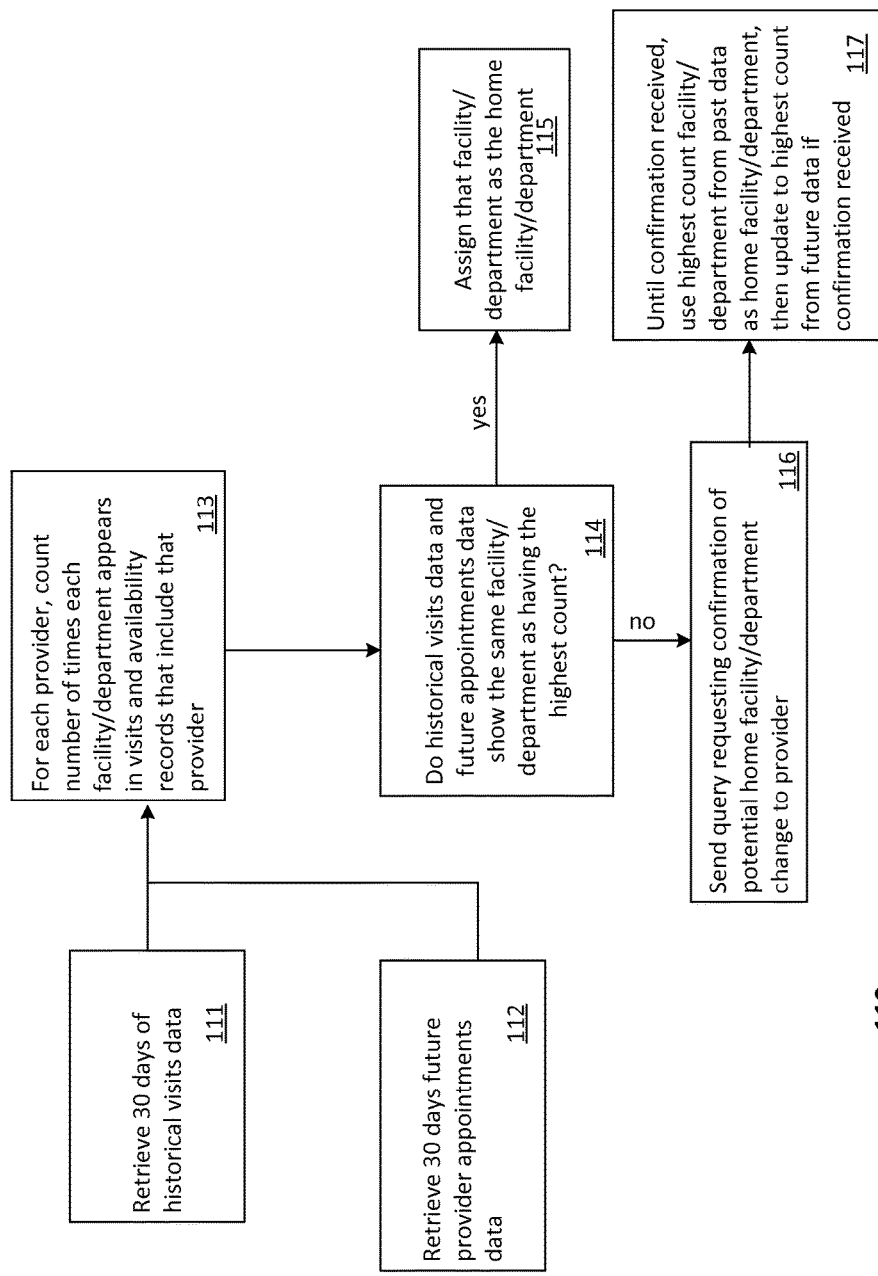
FIG. 11 illustrates an exemplary process carried out by the data flow engine of the embodiment of FIG. 1 including steps for identifying a home facility and home department for a provider.

FIG. 11 illustrates an exemplary process 110 carried out by data flow engine 1400 of the embodiment of FIG. 1.

Process 110 includes steps for identifying a home facility and home department for a provider. In one embodiment, this is useful for identifying a facility and department to associate with calls and emails. Unlike visits data, which have the relevant location of the visit already included in the data, the location for calls and email data may not be relevant for purposes of looking at operational data for a facility, department, and/or module. For example, an email or call might arrive at a central location and/or be responded to from a location outside of the provider's office and department. In these cases, the email and call transaction itself might not capture a relevant location. In some embodiments, a provider home location (e.g., a department/facility) may be provided as an entry in a provider database. Such a location may be useful and could be used for assigning a provider location to associate with call and email data. However, such fixed entries may reflect information that is not accurate or is out of date. For example, when the provider joined the organization, he or she may have been assigned a particular location (facility) and department. However, over time the provider might in fact be seeing patients primarily at other locations and/or in other departments. Therefore, for purposes of assigning accurate location information in support of near real time care optimization, process 110 utilizes recent visits data and near future appointments data to assign a home facility and department.

Step 111 retrieves 30 days of historical visits data. Step 112 retrieves 30 days of future appointments data. Step 113 counts, for each provider, the number of times each facility/department appears for past visits (30 days) and future appointments (30 days) that include that provider. Step 114 determines whether the facility/department with the highest count for a provider's visits in the last 30 days matched the facility/department with the highest count for a provider's next 30 days of scheduled appointments. If yes, then step 115 assigns that facility/department as the home facility/department. If not, then step 116 sends a query requesting confirmation from the provider of a potential home facility change. Step 117 uses the facility/department result based on the past 30 days of visits data until confirmation of a change is received. Once such confirmation is received, step 117 uses the result indicated by the future appointments data. In one embodiment, after such a confirmation, the confirmed result is used for a pre-defined period of time (e.g., 30 days) and then the method reverts to the indicated steps.

Figure 12:
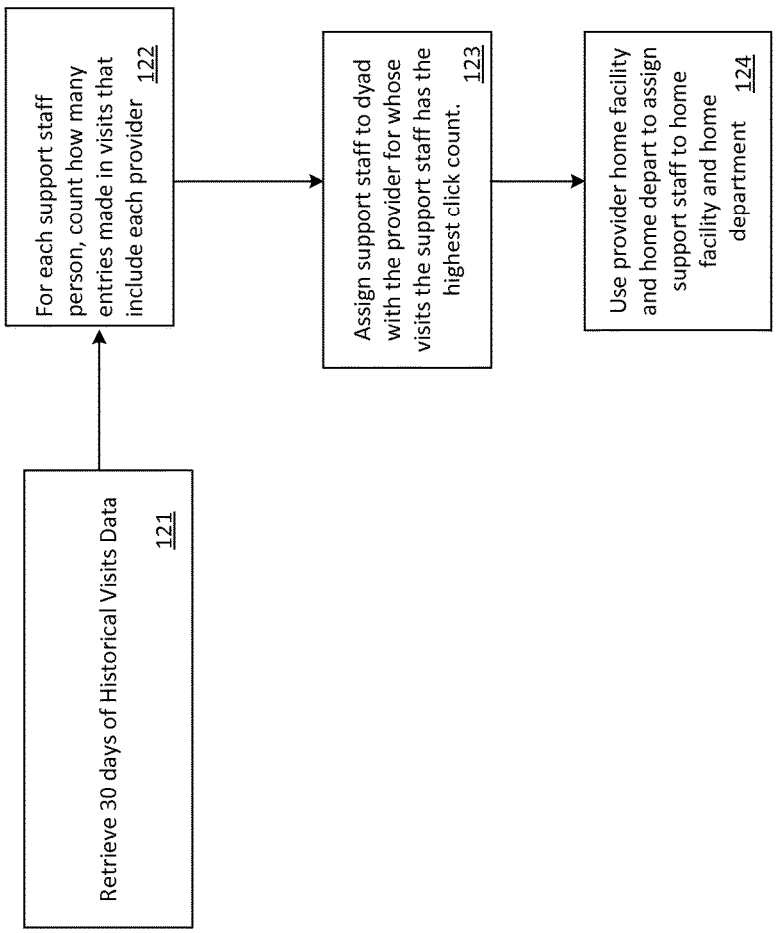
FIG. 12 illustrates an exemplary process carried out by the data flow engine of the embodiment of FIG. 1 including steps for identifying dyad relationships between a provider and a support staff person such as an LPN or an MA.

FIG. 12 illustrates an exemplary process 120 carried out by the data flow engine of the embodiment of FIG. 1. In particular, process 120 includes steps for identifying dyad relationships between a provider and a support staff person such as an LPN or an MA. In an integrated health care enterprise, LPNs and MAs may move frequently from facility to facility and department to department. Therefore, identifying an appropriate "home" facility and "home" department for LPNs and MAs can be even more difficult than making those determinations for providers. In the method illustrated in FIG. 12, the recent visits data is used to identify a dyad relationship and then the home facility and department of the identified provider is used to assign a home facility and department to the support staff person for purposes of an embodiment of the invention.

Step 121 retrieves 30 days of historical visits data. For each support staff person, step 122 counts the number of entries made in the visits that include a particular provider. Step 123 ranks the providers associated with the staff person (e.g., LPN or MA) based on these entries ("click count") and assigns the support staff person to a dyad including the provider for whom the support staff person has most associated visit clicks. Step 124 then uses that provider's home facility and department as the assigned home facility and department for that support staff person.

Figure 13:
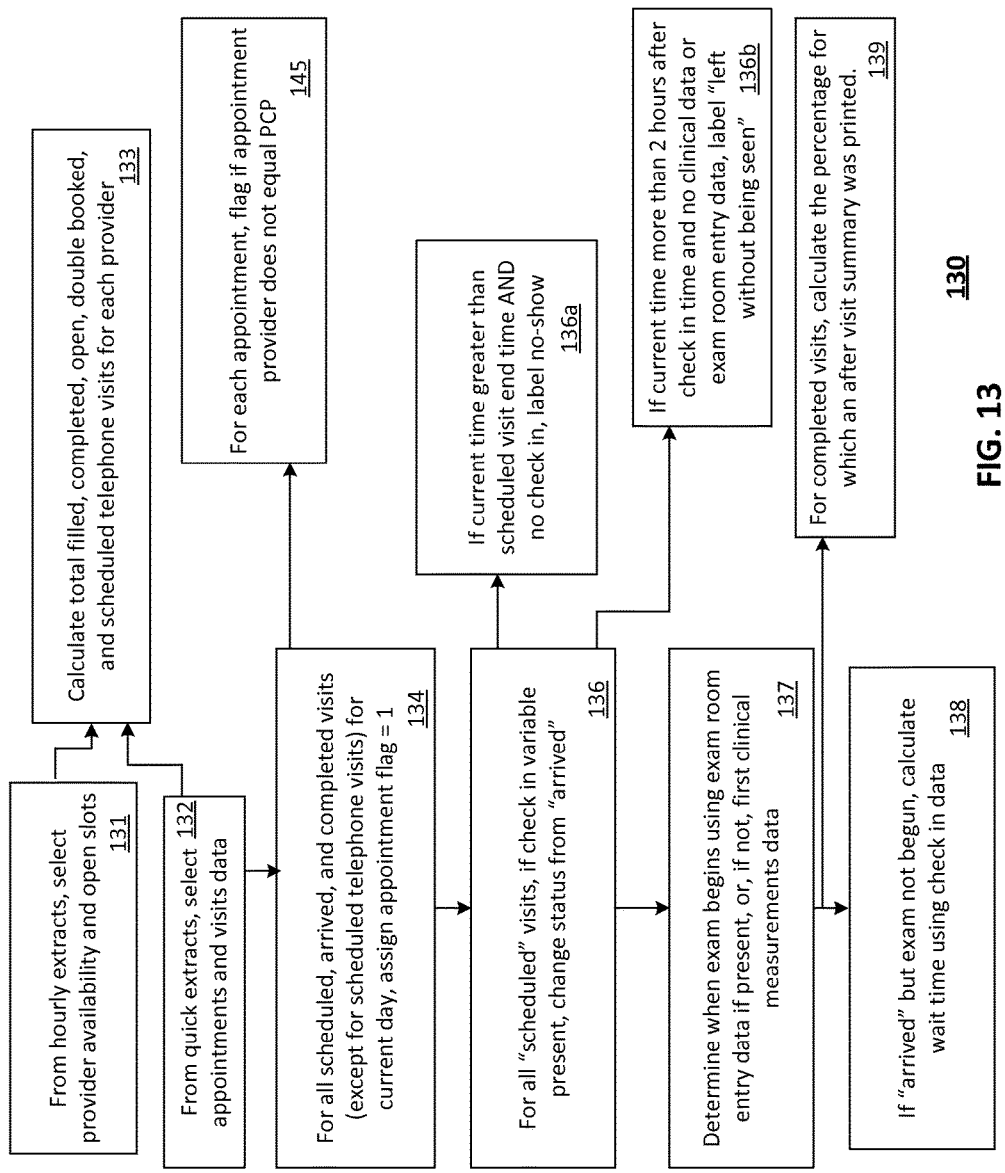
FIG. 13 illustrates an exemplary process carried out by the data flow engine of the embodiment of FIG. 1 including steps for preparing certain of the data used in the "visits" tab illustrated in FIG. 21 and the visits portion of the "overview" tab of FIG. 19.

FIG. 13 illustrates an exemplary process 130 carried out by the data flow engine 1400 of the embodiment of FIG. 1. In particular, process 130 includes steps for preparing certain of the data used in the "visits" tab illustrated in FIG. 21 and the visits portion of the "overview" tab of FIG. 19.

Step 131 selects provider availability and open slots data from the "hourly 1" extract of FIG. 2 (stored in data staging tables 1201). Step 132 selects today's appointments and visits data from the "quick" extract of FIG. 2 (stored in data staging tables 1202). Step 133 uses data from step 131 and 132 to calculate, for each provider, the total filled, completed, open, and double-booked appointments as well as the telephone appointment visits ("TAV").

Step 134 uses data from step 132 to uses an "appointments" flag to designate all visits with a status of scheduled, arrived, or completed (but scheduled telephone visits not given this flag). Step 136 changes the visit status from "scheduled" to "arrived" if appropriate check-in data is present. If the current time is past the scheduled end time of the visit and there is no data indicating check-in, then step 136a labels the visit "no-show." If the data indicates the patient has checked in but there is no clinical data or exam room entry data and the time is more than two hours after check in, then step 136b labels the visit: "left without being seen." Step 137 determines whether and when the visit has begun using an exam room data entry if present, or, if not present, using entry of any clinical tasks data (e.g., blood pressure, weight, etc.). If the visit status is arrived but step 137 has determined that the exam has not begun, then the patient is considered in the waiting room and step 138 calculates the wait time using current time and check in time data. Step 139 determines the percentage of completed visits for which an after visit summary ("AVS") was printed (for giving to the patient).

Figure 14:
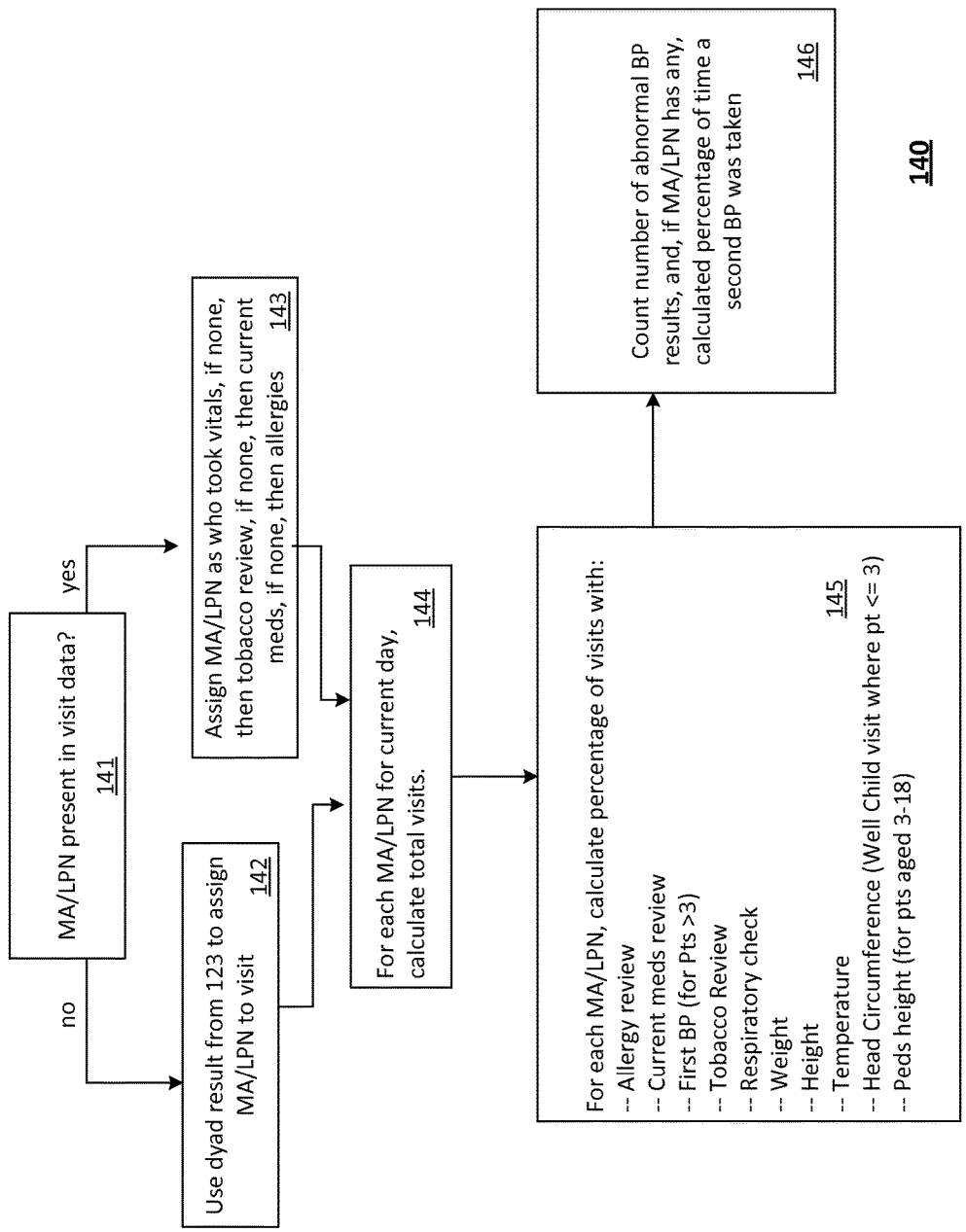
FIG. 14 illustrates an exemplary process carried out by the data flow engine of the embodiment of FIG. 1 including steps for preparing certain of the data used in the "support" tab illustrated in FIG. 24 and in the support portion of the "overview" tab of FIG. 19.

FIG. 14 illustrates an exemplary process 140 carried out by the data flow engine 1400 of the embodiment of FIG. 1. In particular, process 140 includes steps for preparing certain of the data used in the "support" tab illustrated in FIG. 24 and in the support portion of the "overview" tab of FIG. 19.

Step 141 determines, for each of the current day's visits, if a support person (e.g., MA/LPN) is present in the visits data. If yes, then step 143 associates the visit with the MA or LPN who recorded vitals. If a provider name is seen there (instead of an MA or LPN), then step 143 uses the MA/LPN who reviewed smoking history; if no MA/LPN name is seen for smoking history, then step 143 uses the MA/LPN who reviewed allergy history. If no MA/LPN name is seen for any of these locations in the record, then step 142 uses the dyad result from step 123 of FIG. 12 an associates the visit with the support staff person in the visit provider's dyad. Step 144 calculates, for each MA/LPN, the total completed visits for the current day. Step 145 calculates, for each MA/LPN, the percentage of visits showing completed data for allergy review; current medication review, first blood pressure check (performed on patients age 3 and older); review of tobacco use; respirations check; weight measurement; height measurement; temperature measurement; head circumference measurement (only performed for child patients age 3 or under); and height (for children age 3-18). Step 146 counts the number of abnormal readings for the first blood pressure check and, if the MA/LPN has any, step 146 calculates the percentage of the time a second blood pressure check was performed.

Figure 15:
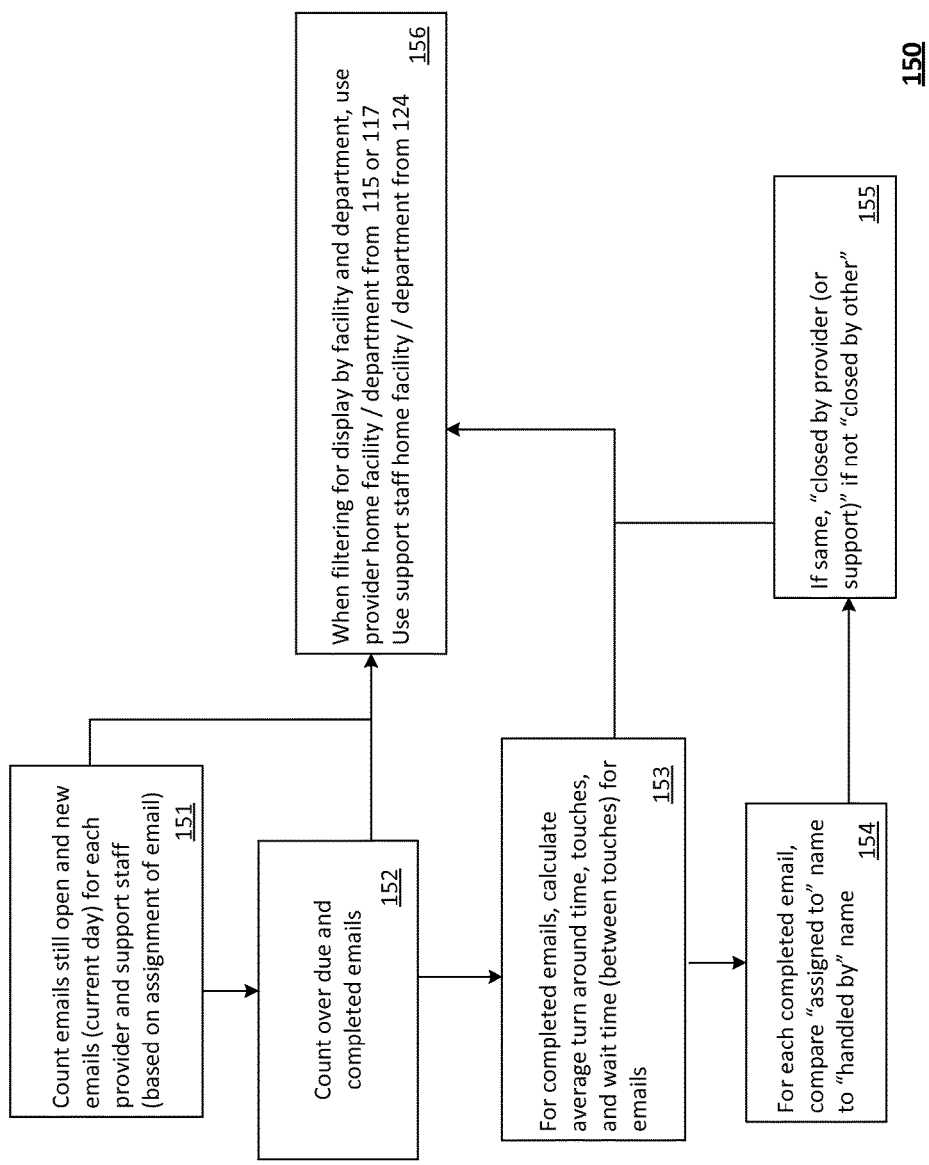
FIGS. 15-16 illustrate exemplary processes carried out by the data flow engine of the embodiment of FIG. 1 including steps for preparing certain of the data used in the "calls/emails" tab illustrated in FIG. 23 and in the calls/emails portion of the "overview" tab of FIG. 19.
Figure 16:
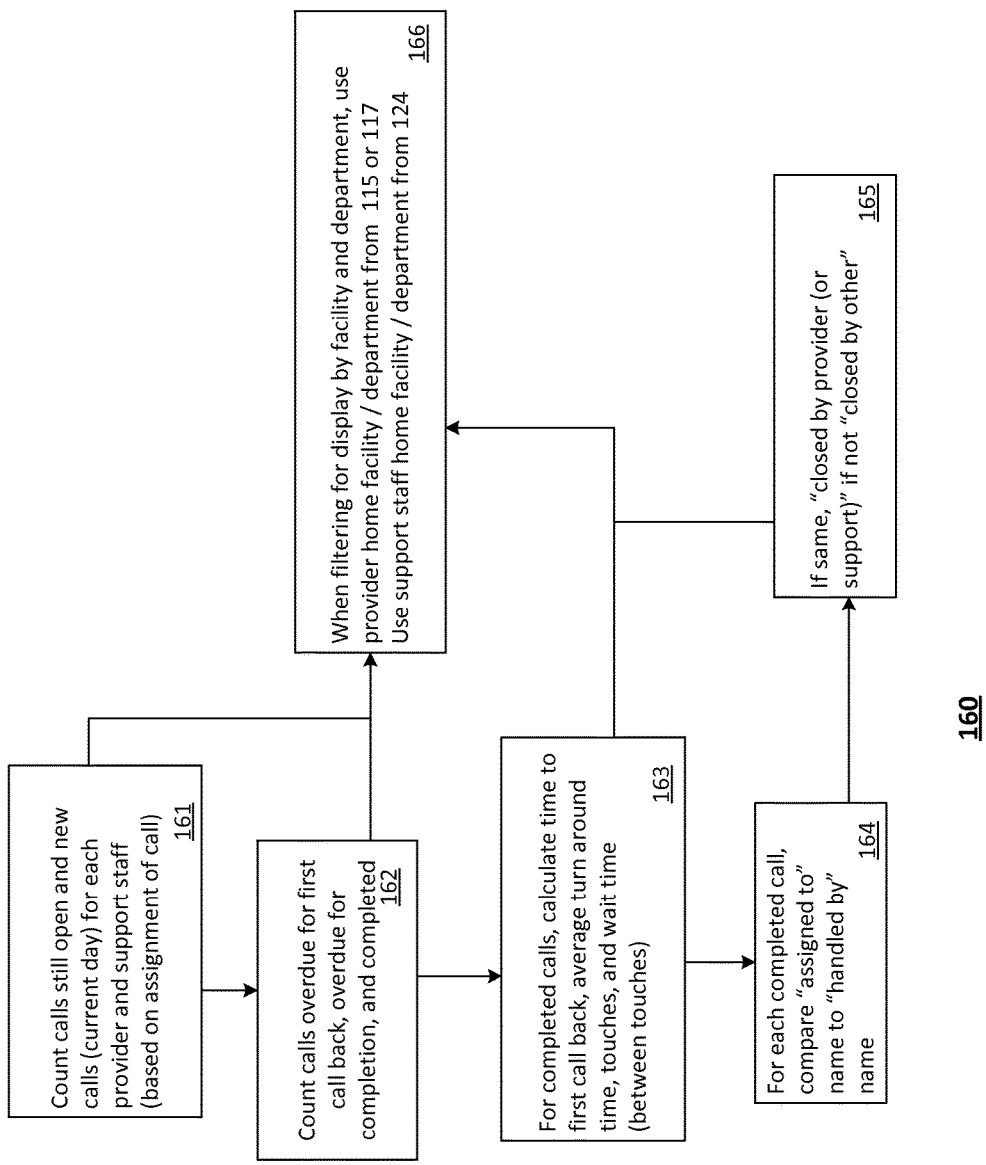

FIGS. 15-16 illustrate an exemplary processes 150 (FIG. 15) and 160 (FIG. 16) carried out by the data flow engine 1400 of the embodiment of FIG. 1. In particular, processes 150 and 160 includes steps for preparing certain of the data used in the "calls/email" tab illustrated in FIG. 23 and in the calls/emails portion of the "overview" tab of FIG. 19. The calls and email data received by data staging tables 1203 and extracted by "hourly 2" extraction module 1830 (both shown in FIG. 2) includes data regarding whether a call or email is resolved or not resolved (referred to as "open" if not resolved). This data generally results from entries made in the EMR system by providers or other staff who handle the call or email.

Referring to process 150 of FIG. 15, step 151 counts the emails that are still open as of the last business day and that are new since the last business day for each provider and support staff based on assignment of the email. Step 152 counts the over due and completed emails. Step 156 uses the provider home facility and department determined in step 115 or 117 of FIG. 11 and the support staff home facility and department determined in step 124 of FIG. 12 to display the email in the calls/emails tab illustrated in FIG. 23. Step 153 calculates average turnaround time, touches, and wait time (between touches) for each provider or support staff's resolved emails. "Touches" refers to separate entries in the email record by individuals handling the email. Step 154 determines if the person handling the email (i.e., resolving it) is the same person the email was assigned to. If the same, then 155 labels the email as "closed by provider" (or support person handing the email). If not the same, the 155 labels the email as closed by other.

Referring to process 160 of FIG. 16, step 161 counts the calls that are still open as of the last business day and that are new since the last business day for each provider and support staff based on assignment of the email. Step 162 counts the calls that are overdue for a first call back, overdue for completion, and that are completed (completed during the current day). Step 166 uses the provider home facility and department determined in step 115 or 117 of FIG. 11 and the support staff home facility and department determined in step 124 of FIG. 12 to display the call in the calls/emails tab illustrated in FIG. 23. Step 163 calculates the average time to a first call back (e.g., to the patient for a patient initiated call), average turnaround time, touches, and wait time (between touches) for each provider or support staffs resolved calls. Step 164 determines if the person handling the call (i.e., resolving it) is the same person the email was assigned to. If the same, then 165 counts the call as "closed by provider" (or support person handing the email). If not the same, the 165 labels the call as closed by other.

Figure 17:
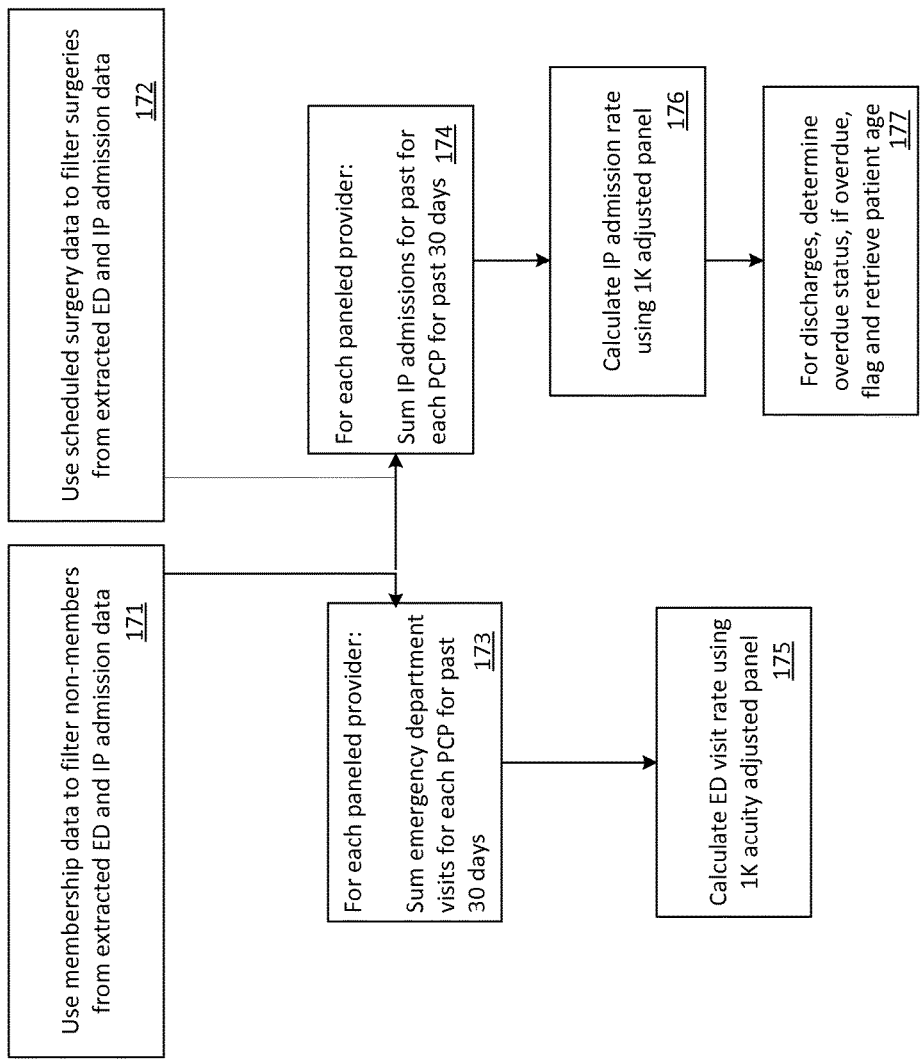
FIG. 17 illustrates an exemplary process carried out by the data flow engine of the embodiment of FIG. 1 including steps for preparing certain of the data used in the emergency department ("ED")/in patient ("IP") tab illustrated in FIG. 25 and in the ED/IP portion of the "overview" tab of FIG. 19.

FIG. 17 illustrates an exemplary process 170 carried out by the data flow engine 1400 of the embodiment of FIG. 1. In particular, process 170 includes steps for preparing certain of the data used in the "ED/IP" tab illustrated in FIG. 25 and in the ED/IP portion of the "overview" tab of FIG. 19.

Step 171 uses membership data to filter non-member records from extracted emergency department ("ED") and in patient ("IP") admissions data. Step 172 uses scheduled surgery data to filter surgeries from extracted ED and IP data. In one embodiment, the purpose of step 172 is so that the data in the ED/IP tab of FIG. 25 (and the ED/IP portion of the overview tab of FIG. 19) more accurately reflects unanticipated ED and IP events for a provider's patient panel. Step 173, for each paneled provider, sums ED visits for the past 30 days for patients in the provider's panel. Step 174, for each paneled provider, sums IP admissions for the past 30 days for patients in the provider's panel. Step 175 uses the results of step 173 to calculate the ED visit rate of each provider's panel based on an adjusted panel size of 1,000. Step 177 uses the results of step 176 to calculate the IP admission rate of each provider's panel based on an acuity adjusted panel size of 1,000.

Figure 18:
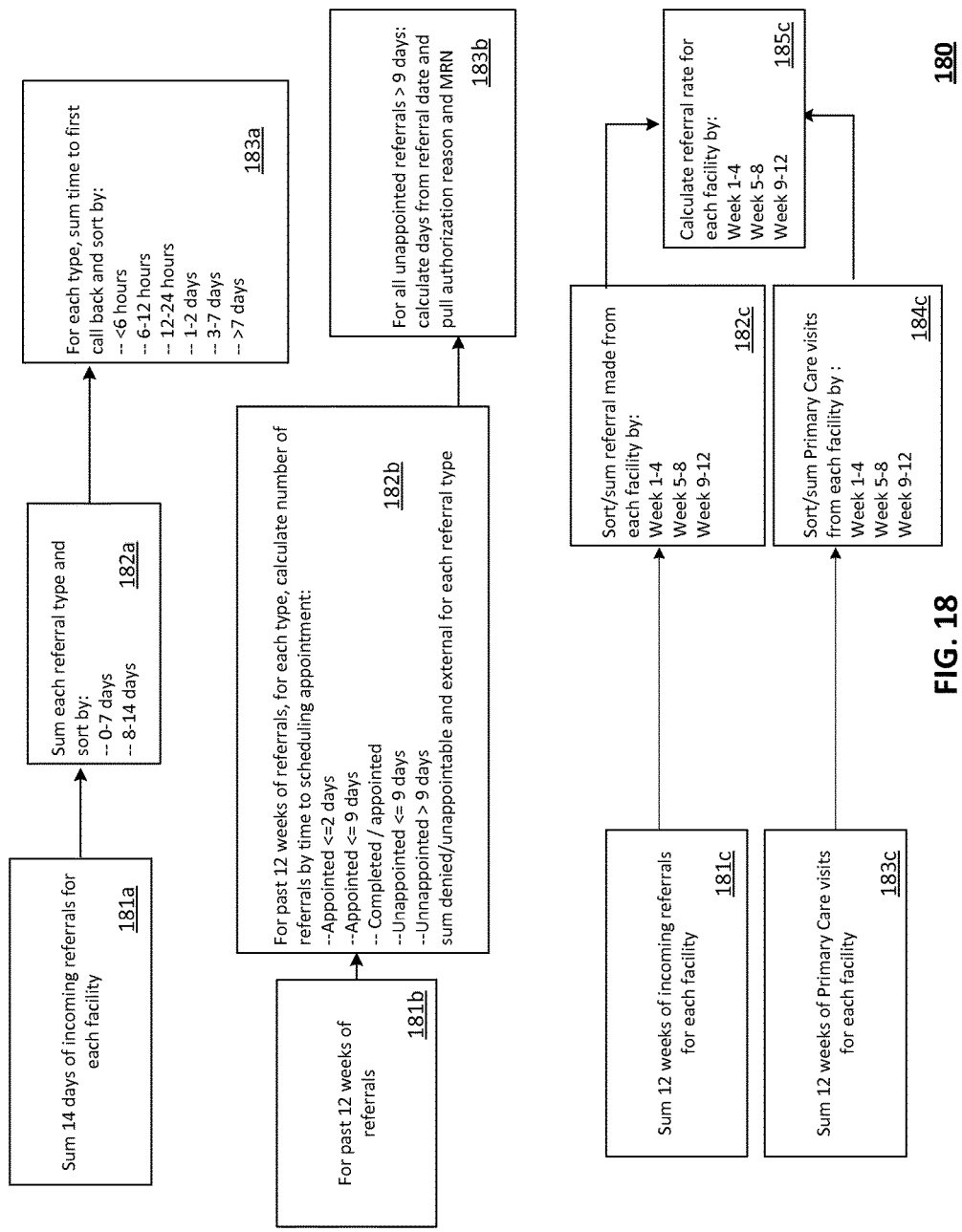
FIG. 18 illustrates an exemplary process carried out by the data flow engine of the embodiment of FIG. 1 including steps for preparing certain of the data used in the specialty care "referrals" tab illustrated in FIG. 27 and in the referrals portion of the specialty care "overview" tab of FIG. 26.

FIG. 18 illustrates an exemplary process 180 carried out by the data flow engine 1400 of the embodiment of FIG. 1. In particular, process 180 includes steps for preparing certain of the data used in the specialty care "referral" tab illustrated in FIG. 27 and in the referral portion of the specialty care "overview" tab of FIG. 26.

Steps 181a-183a use referral data for the past two weeks of incoming referrals. Step 181a sums the incoming referrals from each facility (in one example implementation, the referring department data also indicates a facility name). Step 182a sums each referral type and sorts for display by the following categories: referrals that are 0-7 days old (since being made) and referrals that are 8-14 days old. Step 183a, for each referral type, sums the time to first call back and sorts for display by the following categories: less than 6 hours, 6-12 hours, more than 12 but less than 24 hours, 1-2 days, 3-7 days, and more than 7 days.

Steps 181b-183b use referral data for the past twelve weeks of incoming referrals. Step 181b sums denied/unappointable referrals and external referrals (referrals made by a PCP within the enterprise to a specialty provider outside the enterprise). Step 182b sums the number of appointable referrals for each type, and, uses the time required between the referral being made and an appointment being scheduled—as well as data regarding whether the referral appointment has already been completed—to total and sort for display by the following categories: referrals that are appointed two days or less; referrals that are appointed in 9 days or less; referrals that are completed and/or appointed; referrals that are not appointed and are 9 days old or less; and referrals that not appointed and are more than 9 days old. Step 183b, for all unappointed referrals that are more than 9 days old, pulls for display the authorization reason and the medical record number ("MRN") for each patient.

Step 181c sums 12 weeks of incoming referrals for each facility. Step 182c sorts and sums the number of referrals made by each facility for the following categories: weeks 1-4; weeks 5-8; and weeks 9-12 (where weeks 1-4 are the furthest in the past and 9-12 are the most recent). Step 183c sums 12 weeks of primary care visits for each primary care facility. Step 184c sorts and sums the number of visits by each facility for the following categories: weeks 1-4; weeks 5-8; and weeks 9-12. Step 185c uses the results of 182c and 184c to sort and calculates for display referral rate by each facility for the following categories: weeks 1-4; weeks 5-8; and weeks 9-12.

Figure 19:
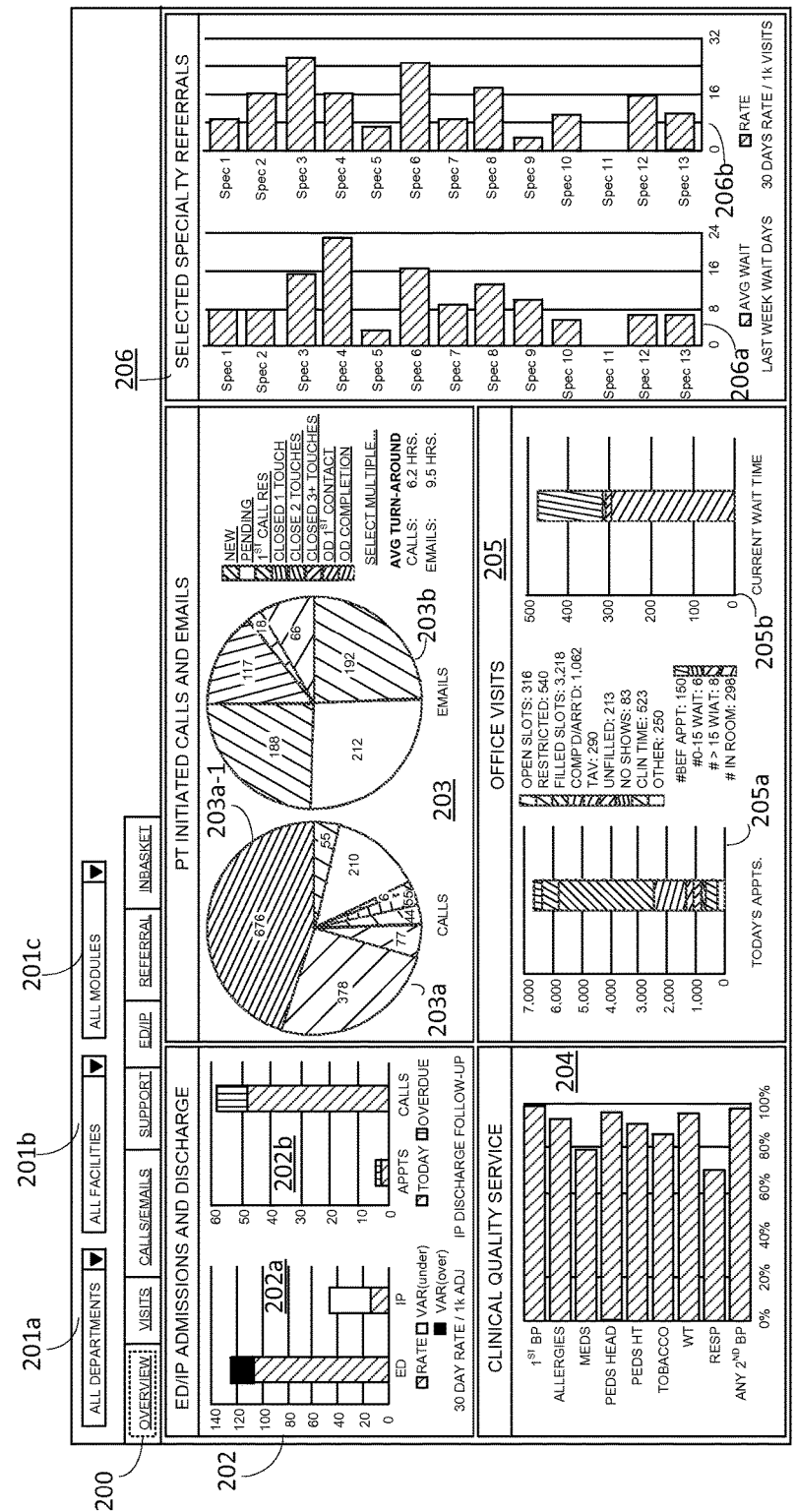
FIG. 19 illustrates an exemplary overview tab of a primary care user interface generated by the embodiment of FIG. 1.

FIG. 19 illustrates an "overview" portion of an exemplary primary care user interface 2000 generated by the embodiment of FIG. 1. As will be appreciated by those skilled in the art, user interface 2000 (like those illustrated in FIGS. 20-27) can be generated by a user device such as user device 1701 of FIG. 1 that interacts with the disclosed system.

Interface portion 2000 comprises a graphical user interface ("GUI") display and includes pull-down menus 201a, 201b, 201c and selectable tabs 200 including "OVERVIEW," "VISITS," "CALLS/EMAILS," "SUPPORT," "ED/IP," and "INBASKET." In this particular view, the tab 200 corresponding to "OVERVIEW" has been selected.

Pull down menus 201a, 201b, and 201c may be used to select particular departments, facilities, and modules. A "module" in this context refers to a particular physical location in a facility and will may or may not correspond to a department. A medium or large integrated health care enterprise will typically have many different facilities and departments. The particular exemplary view in FIG. 20 assumes that all facilities, departments, and modules for primary care have been selected. Primary care departments typically include departments such as family medicine, pediatrics, and internal medicine and may include other departments such as, for example, nurse visits.

Window 202 displays summary data regarding emergency department ("ED") and hospital inpatient ("IP") admissions and IP discharge follow-up. Window 202 includes graphs 202a and 202b. Graph 202a shows the admissions to the emergency room and inpatient (hospital) admissions over the past 30 days per 1,000 patients (e.g. members) of the enterprise. Graph 202b shows follow-up tasks for the current day and to be completed for IP discharges and tasks that are overdue. In particular, a portion of the graph shows, for the current day, the number of discharge follow-up calls that have been made and the number that are overdue, and the number of follow-up appointments that have been scheduled and the number that are overdue. Another portion of graph 202b shows the number of discharge follow-up calls that must be made today and the number that are overdue.

Window 203 displays summary data regarding patient-initiated calls and emails that are either waiting to be resolved or have been resolved for the current day. Pie chart 203a shows the number of calls in various categories: new calls, pending calls, calls that were resolved during the initial call, calls that were resolved after "one touch"—meaning that one staff interaction occurred with the record after the call before it was resolved—, calls that were resolved after two or more touches, calls that are overdue for having a first call back be completed, and calls that are overdue being completed (i.e., fully resolved and closed in the record). For example, portion 203a-1 indicates 676 overdue calls. Pie chart 203b shows similar information for patient initiated emails, except that in this example, emails are generally consider closed once any reply to the patient is completed, therefore "first contact" is not separately tracked from "closed" for emails.

Window 204 summarizes clinical quality service. In particular it shows the percentage of time that certain medical support tasks were completed during office visits. In particular, it shows percentages for: taking a first blood pressure reading; reviewing the patient's allergies; reviewing the patient's current medications; measuring child's head size (for pediatric visits); measuring child's height (for pediatric visits); reviewing the patient's tobacco use/exposure status; doing a respiratory check; measuring the patient's weight; and taking a second blood pressure reading if the first check showed an abnormal result.

Window 205 summarizes office visits for the current day. In particular, graph 203a shows the number of appointment slots that are: open; restricted (i.e., cannot be booked by any appointment representative, but reserved for being booked only under authorization of the provider or other designated individual); filled; completed or for which the patient has arrived; that are telephone appointment visits ("TAV"); that are unfilled (time slot passed without an appointment—"open" slots become "unfilled" after their time passes without being filled); for which the patient did not show up; that represent clinical time set aside by the provider (e.g., for responding to patient calls and emails) that is not available for an appointment; and other (e.g., chart review, extra clinic and travel time, etc.) Graph 203b shows information about patients waiting including the number that are waiting but it is before their appointment time, the number that have been waiting 0-15 minutes and the number that have been waiting more than 15 minutes and the number that are in the exam room ("in room").

Window 206 summarizes referrals made to selected specialties. For each illustrated specialty, graph 206a indicates the average wait time for in days from the issuing of a patient referral to the referral appointment date for which an appointment has been made in the past week. Graph 206b indicates the rate of referrals during the last 30 days made per 1,000 visits for each of the illustrated specialties.

FIG. 20 illustrates a user interface report view 2000-1 that can be accessed by clicking on portion 203a-1 of graph 203a of FIG. 19. In particular, by clicking on portion 203a-1, the detailed report view 2000-1 may be accessed. Detailed report view 2000-1 includes columns 210 of data indicating the contact type (in this case it is a patient initiated call), status, primary care provider name (or other staff assigned as the "owner" of the call), patient medical record number, contact time, department, facility, and module for each of the calls with "overdue completion" status.

Figure 21:
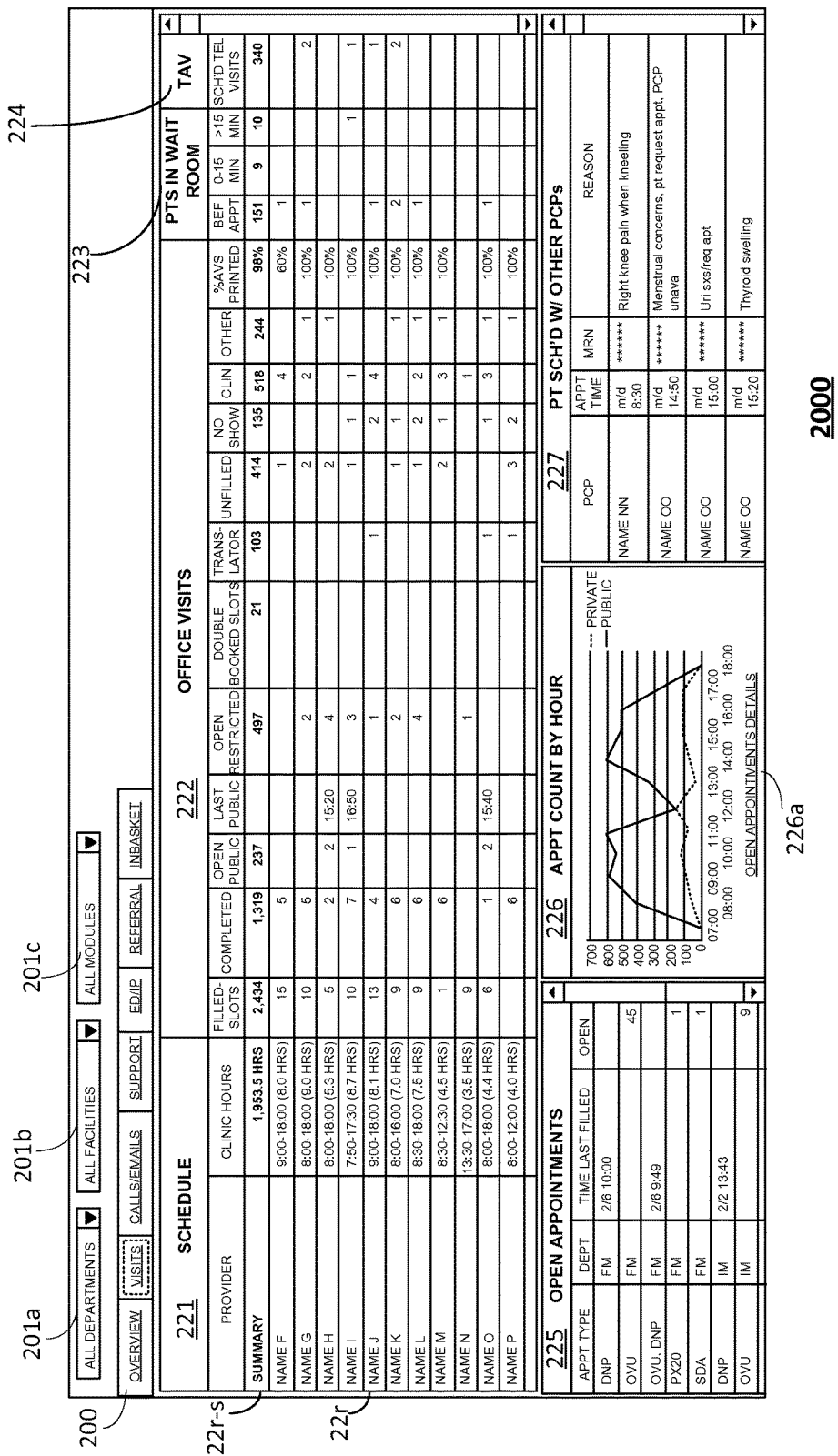
FIG. 21 illustrates an exemplary visits tab of a user interface generated by the embodiment of FIG. 1.

FIG. 21 illustrates another portion of user interface 2000. In particular, FIG. 21 shows a "visits" view of user interface 2000 that is accessible by clicking on the tab 200 labeled "VISITS." As shown, this portion of interface 2000 includes schedule window 221, office visits window 222, waiting room window 223, TAV window 224, open appointments window 225, hourly appointment count window 226, and other provider scheduled window 227.

Windows 221, 222, 223, 224 all display information in relation to summary row 22r-s and individual provider rows 22r. In particular, window 221 displays, for rows 22r, the provider name and scheduled clinic hours for the current day, and for row 22r-s, the total scheduled clinic hours for the selected providers (selected by using pull down menus 201a, 201b, and 201c to select providers by department, facility, and module). Window 222 displays, for each provider in rows 22r, the number of filled slots (i.e., how many appointments are in fact scheduled for each provider); the number of completed appointments, the number of open public appointment slots, the time of the last public appointment slot (i.e., the open public slot with the latest start time); the number of open restricted appointment slots, the number of double-booked slots, the number of slots which are scheduled to have a translator present, the number of unfilled slots (open public and restricted appointment slot that passed by without being filled); the number of no shows; the number of clinical time reserved (and therefore unavailable) slots; the number of other slots; and the percentage of completed visits for which after visit summaries ("AVS") were printed (for giving to the patient after the visit). For row 22r-s, window 222 displays the same information totaled for all providers scheduled that day for the selected facility, module, and department.

Window 223 displays, for each provider in rows 22, the number of patients in the waiting in the following categories: in the waiting room before the scheduled appointment time; waiting between 0-15 minutes; and waiting more than 15 minutes. For row 22r-s, window 223 displays the same information totaled for all providers scheduled that day for the selected department, facility, and module. Window 224 displays, for each provider in rows 22, the number of scheduled telephone appointments. For row 22r-s, window 224 displays the same information totaled for all providers scheduled that day for the selected department, facility, and module.

Window 225 displays open appointments by type, departments, time that the last filled slot was filled, and open.

Window 226 displays a graph showing the number of appointments (public and restricted) each hour during clinic hours. Window 226 also includes link 226a to further details regarding open appointments. Window 227 displays primary care providers with patients that have scheduled appointments for the current day with another primary care provider ("PCP"). It shows the name of the PCP to whom that patient is assigned, the time of the patient's appointment time with the other PCP, the patient's medical record number, and the reason for the appointment.

Figure 22:
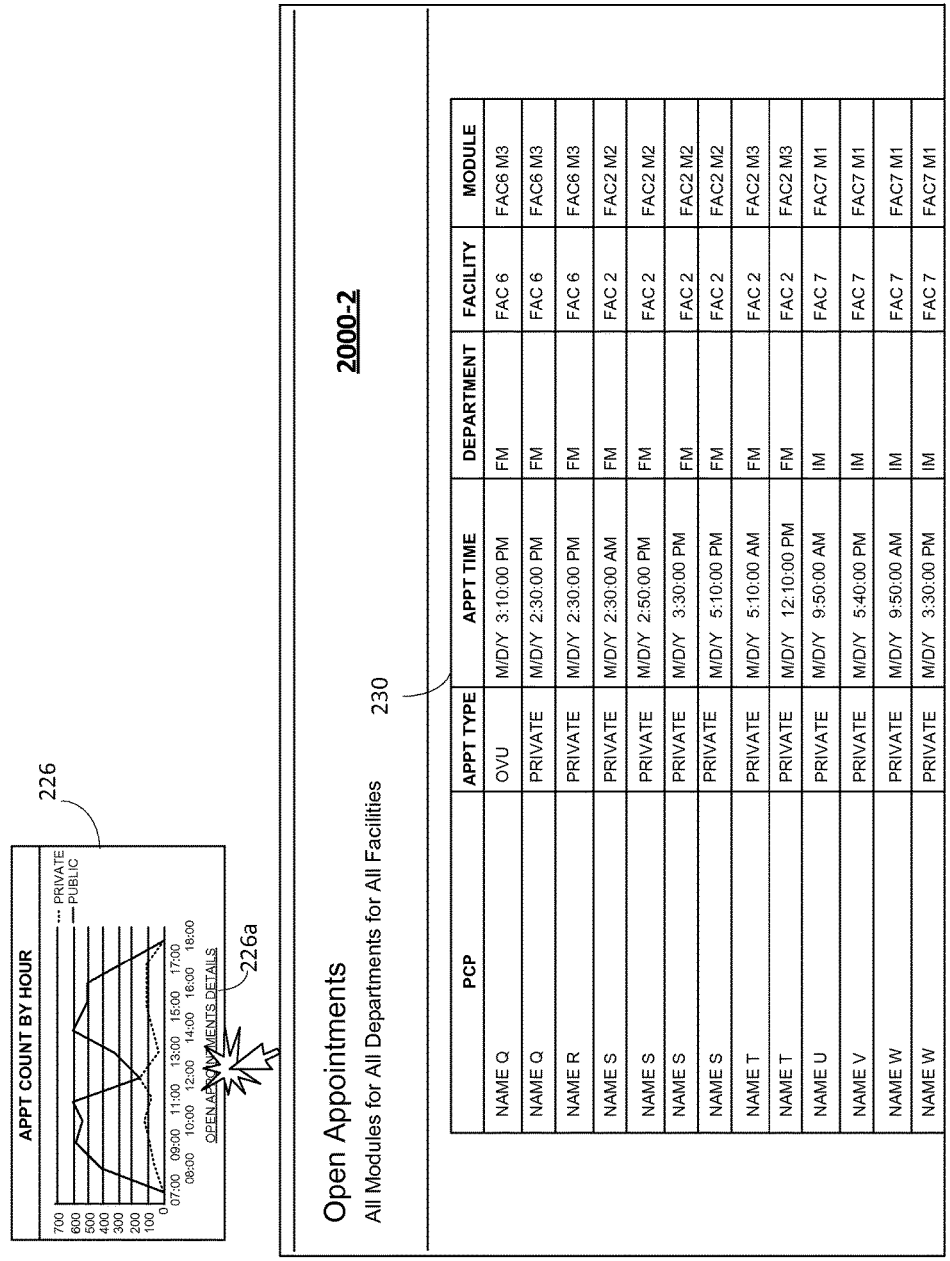
FIG. 22 illustrates an exemplary user interface for a detailed report regarding open appointments accessible from the visits tab of FIG. 21.

FIG. 22 illustrates a user interface report view 2000-2 that can be accessed by clicking on link 226a of window 226 of FIG. 21. In particular, by clicking on link 226a, the detailed report view 2000-2 may be accessed. Detailed report view 2000-2 includes columns 230 of data regarding open appointments indicating the PCP name, the appointment type, the appointment time, the department, facility, and the module.

Figure 23:
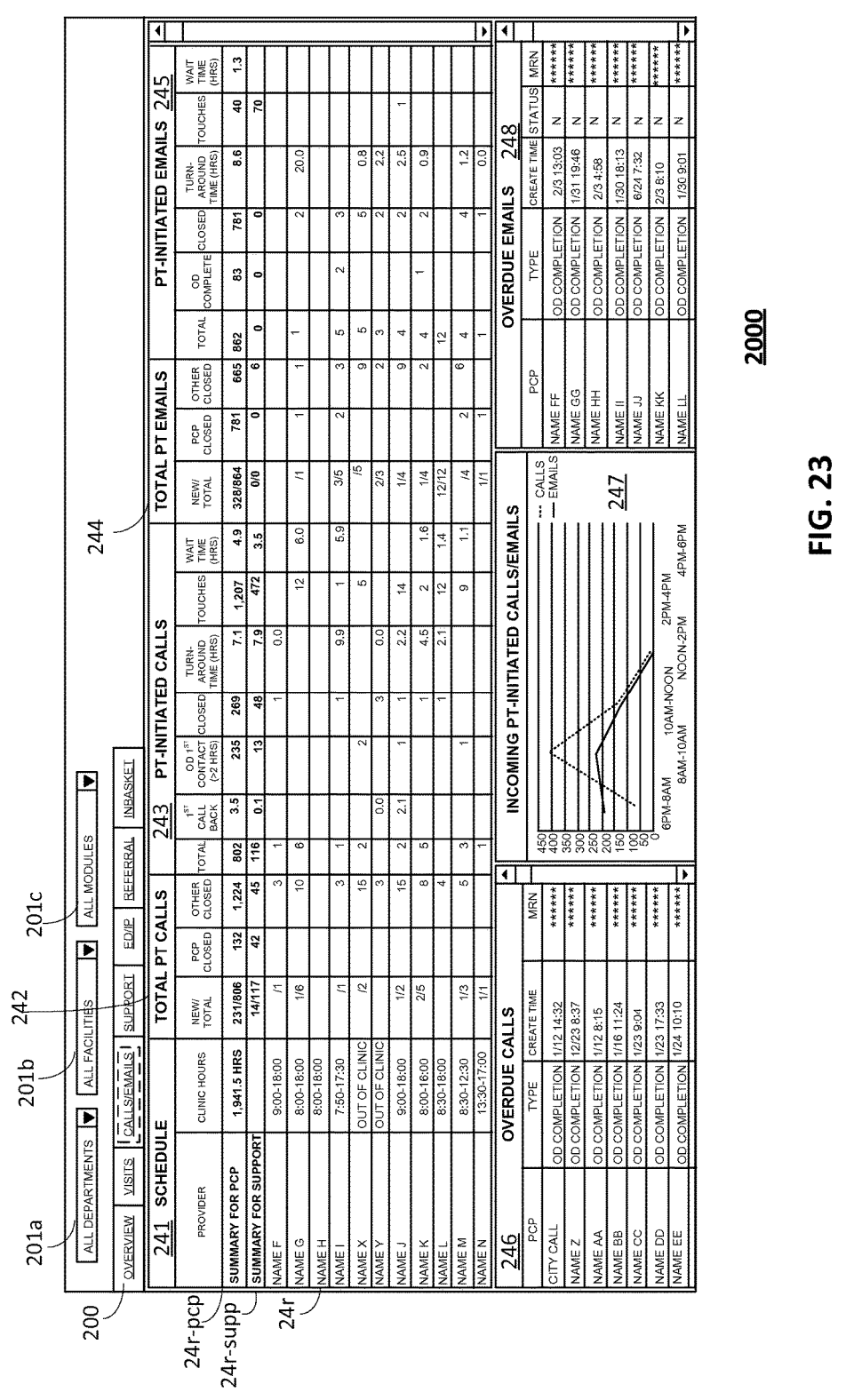

FIG. 23 illustrates another portion of user interface 2000. In particular, FIG. 23 shows a "calls/emails" view of user interface 2000 that is accessible by clicking on the tab 200 labeled "CALLS/EMAILS." As shown, this portion of interface 2000 includes schedule window 241, total patient calls window 242, patient initiated calls window 242, total patient emails 243, patient initiated emails window 245, overdue calls window 246, incoming patient initiated calls/emails window 247, and overdue emails window 248.

Window 241 displays information in relation to PCP summary row 24r-pcp and individual provider rows 24r. In particular, window 241 displays, for rows 24r, the provider name and scheduled clinic hours for the current day, and for row 24r-pcp, the total scheduled clinic hours for the selected providers. Windows 242, 243, 244, and 245 all display information in relation to PCP summary row 24r-pcp, summary row 24r-sup, and individual provider rows 24r.

Windows 242 and 243 display information regarding calls, meaning phone calls that were made and assigned for handling to either a PCP or a support person in the selected department, facility, and module. For each provider in rows 24r, window 242 displays the number of new patient-related calls (for the current day) along with the total number of calls (i.e., all calls that are not yet closed), the number of calls that were closed by the person assigned to the call, and the number of calls that were closed by others. For row 24r-pcp, window 242 displays the number of calls for all PCPs selected and indicates how many PCP calls have been closed by the PCP assigned to the call and how many calls have been closed by others. For row 24r-sup, window 242 displays totals for each of these categories for all support providers. In particular, it indicates how many calls were closed by the support staff person assigned to the call and how many calls were closed by others.

Window 243 displays information about the handing of patient-related calls that were patient-initiated calls. In particular, for individual providers in rows 24r, window 243 displays: the total number of calls (i.e., the number of open calls); the average time it took for a first call back on those calls; the number of calls that are overdue for a first call back (i.e., call back to the patient); the number of calls closed; the average turnaround time (i.e., the time taken to resolve or "close" a call); the number of touches required to close the call, and the wait time—which refers to the time between each touch in handling the call. For row 24r-pcp, window 243 displays the same information, but totaled across all the PCPs in the selected department, facility, and module. For row 24r-supp, window 243 displays the same information, but totaled across all the support staff in the selected department, facility, and module.

Windows 244 and 245 display information regarding emails, meaning emails (which may include messages entered through a web interface) that were sent and assigned for handling to either a PCP or a support person in the selected department, facility, and module. For each provider in rows 24r, window 244 displays the number of new patient-related emails (for the current day) along with the total number of emails (i.e., all emails that have not yet been closed, which in this context, refers to emails that have not yet been replied to), the number of emails that were closed by the person assigned to the email, and the number of emails that were closed by others. For row 24r-pcp, window 244 displays the number of emails for all PCPs selected and indicates how many PCP emails have been closed by the PCP assigned to the email and how many emails have been closed by others. For row 24r-sup, window 244 displays totals for each of these categories for all support providers. In particular, it indicates how many emails were closed by the support staff person assigned to the email and how many emails were closed by others.

Window 245 displays information about the handing of patient-related emails that were patient initiated emails. In particular, for individual providers in rows 24r, window 245 displays the total number of emails, the number of overdue emails (i.e., the number of emails are late in being replied to), the number of closed emails, the average turnaround time, the number of touches and the average wait time between touches. For row 24r-pcp, window 245 displays the same information, but totaled across all the PCPs in the selected department, facility, and module. For row 24r-supp, window 245 displays the same information, but totaled across all the support staff in the selected department, facility, and module.

Window 246 displays, for each overdue call: the PCP; the time the call was created (calls are created when a call agent make an entry for the call in the relevant call transaction system); and the patient's medical record number. Window 247 displays a graph showing the number of incoming patient initiated calls and emails during various time periods including 6 PM-8 AM (i.e., since clinic closing time on the prior day), 8-10 AM, 10 AM-noon, noon-2 PM, 2-4 PM, and 4-6 PM. Window 248 displays, for each overdue email, the PCP, the time the email was received, and the patient's medical record number.

FIG. 24 illustrates another portion of user interface 2000. In particular, FIG. 24 shows a "support" view of user interface 2000 that is accessible by clicking on the tab 200 labeled "SUPPORT." The purpose of this exemplary support view is to show—on a real time or near real time basis—whether and to what extent certain clinical tasks are carried out by medical support personnel (such as MAs and LPNs) at the department/facility/module level and at the level of the individual support person. In particular, the illustrated view includes windows 251, 252, and 253.

Window 251 simply lists the individual support staff by name and indicates whether they are an MA or an LPN. Window 252 lists specific tasks to be performed for the current day's office visits. Specifically, for individual support staff rows 25r, window 252 lists, for each individual provider, total office visits; the percentage of visits in which allergies were reviewed; the percentage of visits in which the patient's current medications were reviewed; the percentage of visits in which a first blood pressure check was performed; the number of times that the first blood pressure check indicated an abnormal reading; the percentage of times that, when the first blood pressure checked indicated an abnormal reading, a second blood pressure check was performed; the percentage of visits in which tobacco use was reviewed; the percentage of visits in which a respiratory check was completed; the percentage of visits in which weight was measured; the percentage of visits in which height was measured (for children ages 3-18); and the percentage of visits in which temperature was taken. For summary row 25r-s, window 252 lists the same information totaled across all the support staff for the selected department, facility, and module.

Window 253 shows information indicating call, email, and letter volume handled by the indicated support staff. In particular, for individual support staff rows 25r, window 253 shows the number of call touches, email touches, and letters sent. For summary row 25r-2, window 253 lists the same information totaled across all the support staff for the selected department, facility, and module.

Figure 25:
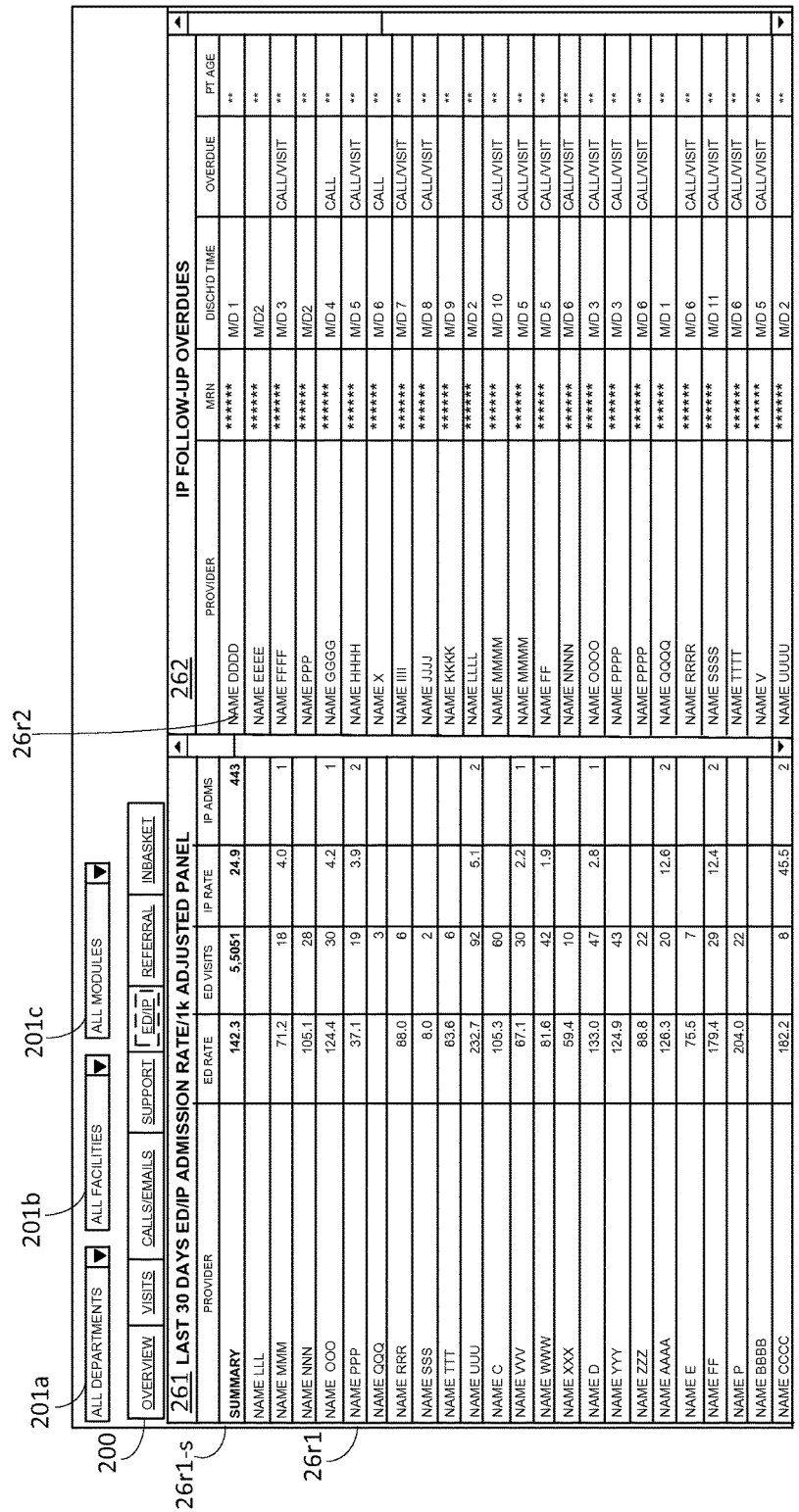
FIG. 25 illustrates an exemplary emergency department/inpatient admission tab of a user interface generated by the embodiment of FIG. 1.

FIG. 25 illustrates another portion of user interface 2000. In particular, FIG. 25 shows an "ED/IP" view of user interface 2000 that is accessible by clicking on the tab 200 labeled "ED/IP." Window 261 shows emergency department and in patient admission rates per 1,000 patients in the provider's panel. ("Panel" refers to the group of patients assigned to a particular provider). In particular, for provider rows 26r, window 261 shows the provider, the emergency department visit rate (per 1,000 adjusted panel size), the total number of emergency department visits, the inpatient admission rate (per 1,000 adjusted panel size), and the total inpatient admissions. In this particular view, the first several provider rows 26r1 show these numbers totaled for particular facilities (note that in this example, "all departments" and "all facilities" are selected by pull down menus 201a and 201b). Beginning with the last several rows 26r1 displayed in FIG. 25, the numbers are shown for individual providers in the selected facilities. For row 26r1-s, the numbers are totaled for all provider panels in the selected facilities, departments, and modules (in this example "all" are selected).

Window 262 lists all the inpatient discharge follow-up tasks that are overdue for providers in the selected facilities, departments, and modules. In particular, for rows 26r2, window 262 shows the provider, the patient medical record number, the time (month and day) that the patient was discharged, the type of follow-up that is overdue, and the age of the patient.

Figure 26:
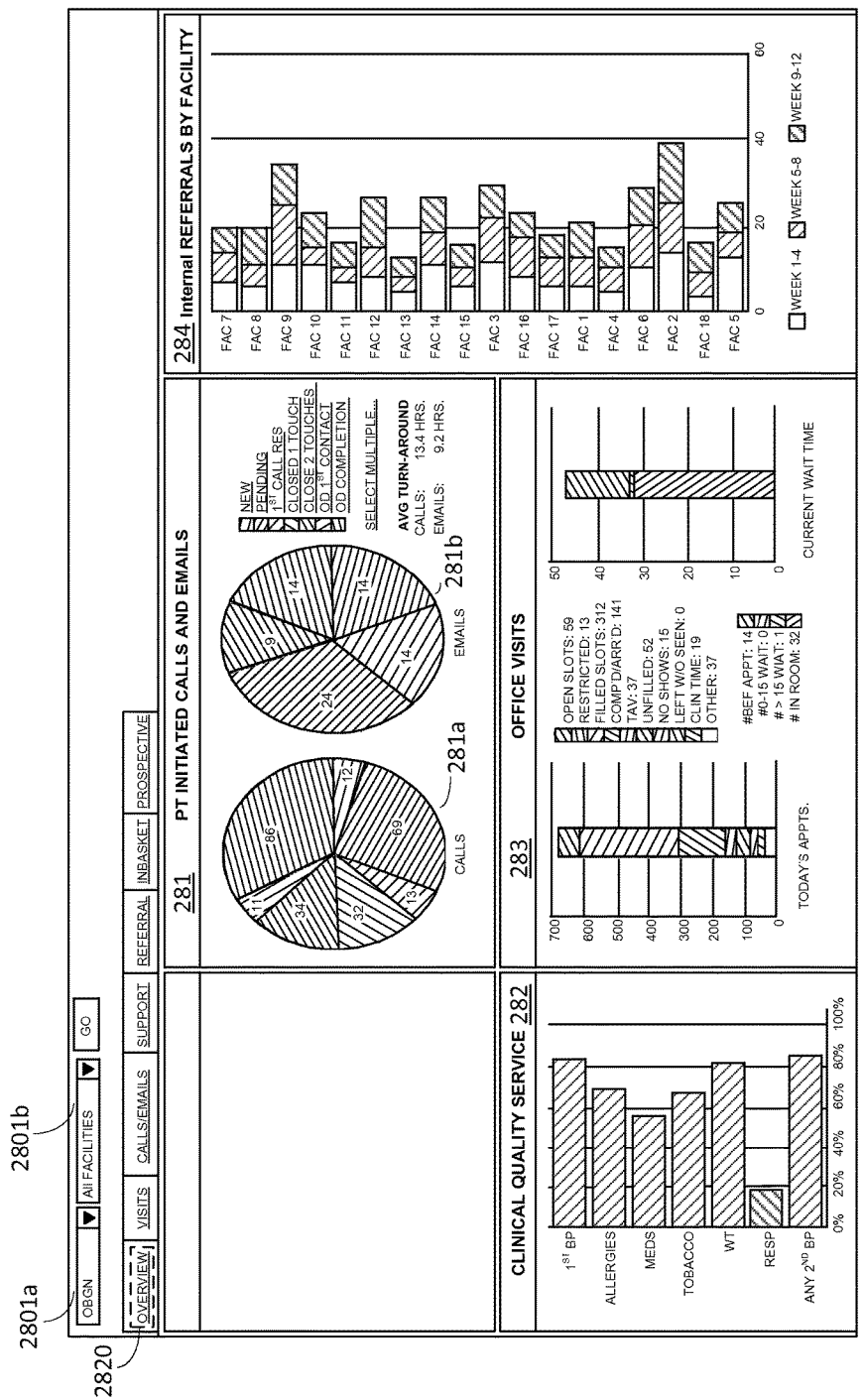
FIG. 26 illustrates an exemplary overview tab for a specialty care user interface generated by the embodiment of FIG. 1.

FIG. 26 illustrates an "overview" portion of an exemplary specialty care user interface 2600 generated by the embodiment of FIG. 1.

Interface portion 2600 comprises a graphical user interface ("GUI") display and includes pull-down menus 2801a and 2801b and selectable tabs 2820 including "OVERVIEW," "VISITS," "CALLS/EMAILS," "SUPPORT," "ED/IP," and "INBASKET." In this particular view, the tab 2820 corresponding to "OVERVIEW" has been selected.

Pull down menus 2801a and 2801b, and 201c may be used to select particular departments and facilities. A medium or large integrated health care enterprise will typically have many different facilities and many different specialty care departments. The particular exemplary view in FIG. 20 assumes that the obstetrics and gynecology department ("OBGN") has been selected. Specialty care typically may include various departments such as cardiology, oncology, dermatology, gastroenterology, and many others.

Window 281 displays summary data regarding patient initiated calls and emails that are either waiting to be resolved or have been resolved for the current day. Pie chart 281a shows the number of calls in various categories: new calls; pending calls; calls that were resolved during the initial call; calls that were resolved after one touch; calls that were resolved after two or more touches; calls that are overdue for having a first call back be completed, and calls that are overdue being completed (i.e., fully resolved and closed in the record). Pie chart 281b shows similar information for patient initiated emails, except that in this example, emails are generally considered closed once any reply to the patient is completed; therefore "first contact" is not separately tracked from "closed" for emails in this particular example.

Window 282 summarizes clinical quality service. In particular it shows the percentage of time that certain medical support tasks were completed during office visits. In particular, it shows percentages for: taking a first blood pressure reading; reviewing the patient's allergies; reviewing the patient's current medications; reviewing the patient's tobacco use; measuring the patient's weight; doing a respiratory check; and taking a second blood pressure reading if the first check showed an abnormal result.

Window 283 summarizes office visits for the current day. It illustrates information substantially similar to that shown in window 205 of the primary care overview tab view of FIG. 19. The associated description will therefore not be repeated hear except to note that the any data generated for a view such as that shown in FIG. 26 would, in an actual implementation, reflect the selection of a particular specialty care department, whereas any data generated for the corresponding view in FIG. 20 would, in an actual implementation, reflect the selection of all primary care departments across multiple facilities.

Window 284 shows a relative overall comparison of referral rates by referring facility for the past 12 weeks. The graph in window 284 further shows the referral rate for each facility (based on referrals per 1,000 visits at each facility) during each 4 week period within those 12 weeks including: weeks 1-4, 5-8, and 9-12.

FIG. 27 illustrates another portion of specialty care user interface 2600. In particular, FIG. 27 shows a "referrals" view of user interface 2600 that is accessible by clicking on the tab 2820 labeled "REFERRALS." As shown, this portion of interface 2600 includes windows 291, 292, 293, and 294. Windows 291 and 292 show data by referral type for each type shown at the left of each row 29r. In particular, window 291 shows the number of incoming referrals by type for the past 2 weeks including the number of incoming referrals in days 8-14 and in days 0-7 for each type. Window 292 shows the number of referrals by type within the last 12 weeks in the following categories: referrals that were appointed (i.e., an appointment was scheduled) in 2 or fewer days (from the date the referral was made); referrals that were appointed in fewer than 7 days; referrals that have been completed or appointed; referrals that have been not been appointed and are 9 days or less old; referral that have not been appointed and are greater than 9 days old; denied or otherwise unappointable referrals; and external referrals.

Window 293 shows selected information for individual referrals made within the past 12 weeks and that have not been appointed for more than 14 days after the referral was made. In particular, for those referrals, window 293 shows the referral type, the MRN, the authorization reason, the number of days from the date the referral was made, and whether the referral was cancelled. Window 294 shows selected information for the time to first call back (i.e., call to patient) for the referrals made in the last two weeks. In particular, for each referral type, window 294 shows the number of referrals in the following categories: time to first call back <6 hours; time to first call back 6-12 hours; time to first call back 12-24 hours; time to first call back 1-2 days; and time to first call back greater than several days.

Figure 28:
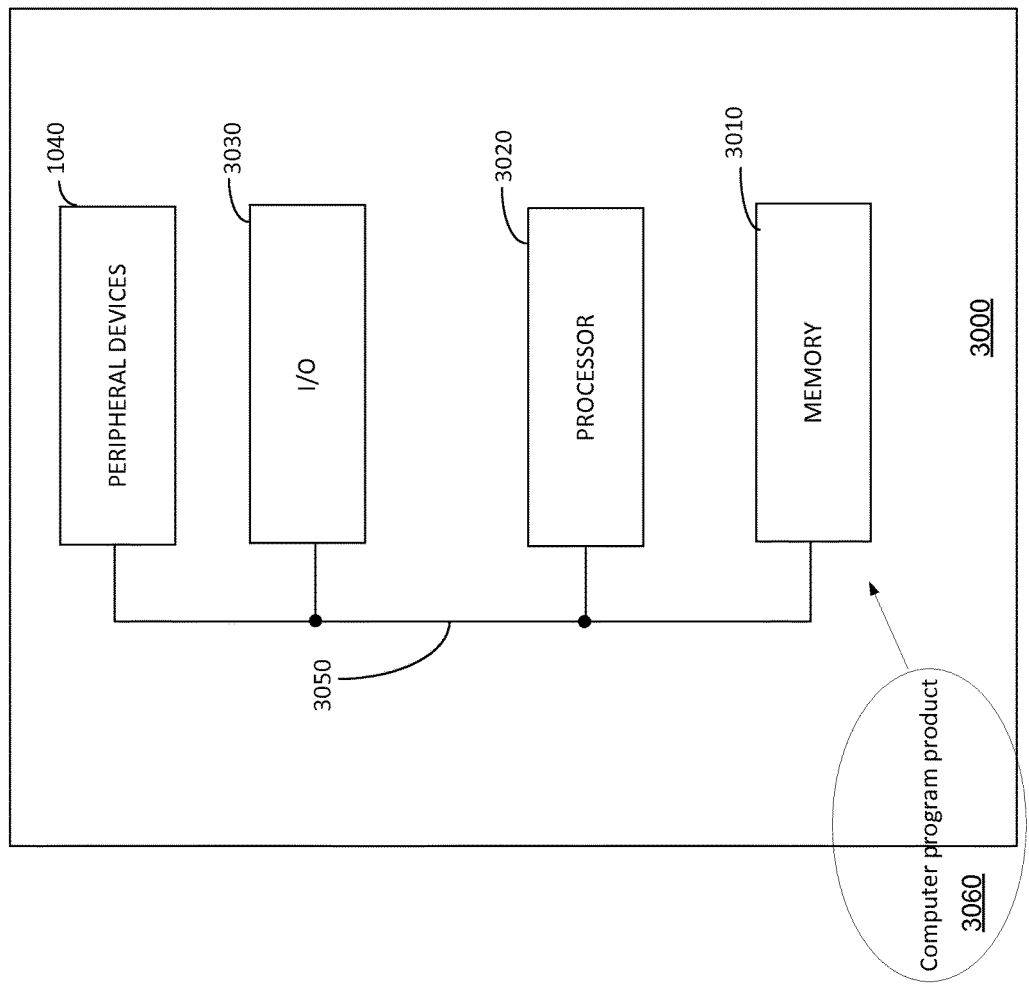
FIG. 28 shows an example of a computer system that may be used to execute instruction code contained in a computer program product, the computer program product being in accordance with an embodiment of the present invention.

FIG. 28 shows an example of a computer system 3000 (one or more of which may provide the components of system 1000 of FIG. 1) that may be used to execute instruction code contained in a computer program product 3060 in accordance with an embodiment of the present invention. Computer program product 3060 comprises executable code in an electronically readable medium that may instruct one or more computers such as computer system 3000 to perform processing that accomplishes the exemplary method steps performed by the embodiments referenced herein. The electronically readable medium may be any non-transitory medium that stores information electronically and may be accessed locally or remotely, for example via a network connection. The medium may include a plurality of geographically dispersed media each configured to store different parts of the executable code at different locations and/or at different times. The executable instruction code in an electronically readable medium directs the illustrated computer system 3000 to carry out various exemplary tasks described herein. The executable code for directing the carrying out of tasks described herein would be typically realized in software. However, it will be appreciated by those skilled in the art, that computers or other electronic devices might utilize code realized in hardware to perform many or all of the identified tasks without departing from the present invention. Those skilled in the art will understand that many variations on executable code may be found that implement exemplary methods within the spirit and the scope of the present invention.

The code or a copy of the code contained in computer program product 3060 may reside in one or more storage persistent media (not separately shown) communicatively coupled to system 3000 for loading and storage in memory 3010 for execution by processor 3020. Computer system 3000 also includes I/O subsystem 3030 and peripheral devices 3040. I/O subsystem 3030, peripheral devices 3040, processor 3020, and memory 3010 are coupled via bus 3050.

Those skilled in the art will appreciate computer system 3000 illustrates just one example of a system in which a computer program product in accordance with an embodiment of the present invention may be implemented. To cite but one example of an alternative embodiment, execution of instructions contained in a computer program product in accordance with an embodiment of the present invention may be distributed over multiple computers, such as, for example, over the computers of a distributed computing network.

Additional Embodiments

Computer System for Health Care Delivery Operational Intelligence

In a first embodiment, a health care delivery operational data computer system comprising: a computer implemented user interface engine communicatively coupled to a data mart and configured to send data from the data mart for display by a computerized graphical user interface; and a computer implemented data flow engine configured to (i) receive selectively extracted data from one or more computerized medical information database systems and (ii) use the selectively extracted data to populate the data mart; wherein: the data flow engine is operable to provide health care delivery data to the data mart and the user interface engine is operable to selectively deliver displayable data of the health care deliver data to an end user device, the displayable data including, for each of a plurality of medical providers: schedule data including clinic times of the provider for the current day; visits data including data regarding a number of appoint slots filled, completed, and open for the current day; and communications data including data regarding patient-initiated communications.

A second embodiment comprising the system of the first embodiment wherein the communications data includes data regarding how many of the patient-initiated communications are new for the current day and how many of the patient-initiated communications are pending as of the current time.

A third embodiment comprising the system of the first embodiment wherein the communications data includes data regarding a number of patient-initiated communications resolved during the current day.

A fourth embodiment comprising, the system of the third embodiment wherein the communications data includes data regarding whether communications were resolved by an assigned person or by another person.

A fifth embodiment comprising, the system of the third embodiment wherein the communications data includes data regarding a turnaround time for resolving the resolved patient-initiated communications.

A sixth embodiment comprising, the system of the first embodiment wherein the communications data includes data regarding a number of patient-initiated communications that are overdue being resolved.

A seventh embodiment comprising, the system of the third embodiment wherein the communication data includes data regarding patient-initiated calls and further includes data regarding a number of separate entries ("touches") in a record of the patient-initiated call.

An eighth embodiment comprising, the system of the third embodiment wherein the communication data includes data regarding patient initiated calls and further includes data regarding an average time for a first call back be in response to patient-initiated calls.

A ninth embodiment comprising, the system of the third embodiment wherein the communication data includes data regarding patient-initiated electronic messages.

A tenth embodiment comprising, the system of the first embodiment wherein the data mart is operable to provide, and the user interface engine is operable to display, medical support staff data including, for each of a plurality of medical support staff: clinical quality data including data regarding completion by a medical support staff of selected clinical support tasks during patient visits for the current day.

An eleventh embodiment comprising, the system of the tenth embodiment wherein the clinical support tasks include two or more of: a first blood pressure check; an allergy review; a medication review; a tobacco review; a weight measurement; and a temperature measurement.

A twelfth embodiment comprising, the system of the first embodiment wherein the data flow engine is operable to provide medical care delivery data to the data mart and the user interface engine is operable to selectively cause display of medical care delivery data that further includes, for each of a plurality of medical providers: in-patient admissions data indicating in-patient admissions for a panel of the medical provider during a selected time period.

A thirteenth embodiment comprising, the system of the first embodiment wherein the data flow engine is operable to provide medical care delivery data to the data mart and the user interface engine is operable to selectively cause display of medical care delivery data that further includes, for each of a plurality of medical providers: emergency department data indicating emergency department visits for a panel of the medical provider during a selected time period.

A fourteenth embodiment comprising, the system of the first embodiment wherein the data flow engine is operable to provide medical care delivery data to the data mart and the user interface engine is operable to selectively cause display of medical care delivery data that further includes, for each of a plurality of medical providers: discharge follow-up data including a list of hospital discharges that have an overdue follow-up task as of the current day.

A fifteenth embodiment comprising, the system of the fourteenth embodiment wherein the discharge follow-up data further includes, for each of a plurality of discharges on the list, a discharge date and a patient identifier.

A sixteenth embodiment comprising, the system of the first embodiment wherein the data flow engine is operable to provide the medical care delivery data for display by the user interface for medical providers across a user-selected aggregation of one or more primary care departments.

A seventeenth embodiment comprising, the system of the sixteenth embodiment wherein the primary care departments include one or more of a family practice department, a pediatrics department, and an internal medicine department.

An eighteenth embodiment comprising, the system of the first embodiment wherein the data flow engine is operable to provide the medical care delivery data for display by the user interface for medical providers across a user-selected aggregation of one or more specialty care departments.

A nineteenth embodiment comprising, the system of the first embodiment wherein the data flow engine is configured to: receive refreshed first data sets from the one or more computerized medical information database systems on a first refresh schedule have a first frequency of greater than once per hour during at least a portion of an operational day; receive refreshed second data sets from the one or more computerized medical information database systems on a second refresh schedule having a second frequency; and use the first refreshed data sets to refresh first data in the data mart on a schedule having the first frequency and to refresh second data in the data mart on a schedule having the second frequency.

A twentieth embodiment comprising, a computer implemented method for providing a health care delivery optimization dashboard interface on a user computer, the method comprising: receiving at one or more computers health care delivery data including at least first and second health care delivery data from one or more medical information database systems wherein receiving comprises receiving first health care delivery data on a first schedule and receiving second health care deliver data on a second schedule, the first schedule having a receive frequency of more than once per hour, the second schedule having a receive frequency that is less than the receive frequency of the first schedule; and configuring, using the one or more computers, the health care delivery data as displayable data for display by an end user device; and using the one or more computers to electronically send requested portions of the displayable data for display by the end user device, the displayable data including, for each of a plurality of medical providers: schedule data including clinic times of the provider for the current day; visits data including data regarding a number of appoint slots filled, completed, and open for the current day; and communications data including data regarding patient-initiated communications; wherein the health care delivery data includes data regarding health care delivery at a plurality of medical departments and facilities and configuring includes associating the medical providers with a medical facility and department such that the displayable data is displayable by medical facility and department.

A twenty-first embodiment comprising, the method of the twentieth embodiment wherein the first health care delivery data includes current day visits and appointments data and the second health care delivery data includes patient-initiated calls and electronic message data.

A twenty-second embodiment comprising, the method of the twentieth embodiment wherein receiving the health care delivery data further comprises third data and receiving further comprises receiving the third data on a third schedule, the third schedule having a receive frequency that is less than the receive frequency of the second schedule.

A twenty-third embodiment comprising, the method of the twenty-second embodiment wherein the first health care delivery data includes ED/IP admissions and IP discharge data.

A twenty-fourth embodiment comprising, a computer implemented method for providing a health care delivery optimization dashboard interface on a user computer, the method comprising: receiving at one or more computers health care delivery data including at least visits data, provider data, support staff data, and patient communications data, the visits data including historical visits data, future appointments data, and current day visits data, at least some of the visits data including, for each of a plurality of visits or appointments, a provider for the visit or appointment, a facility and/or department ("facility/department") for the provider, and, for at least some of the historical visits data further including, for each of a plurality of historical visits, a support staff person associated with or performing tasks during a visit or appointment; calculating, using the one more computers, for each of a plurality of providers, the number of times each of one or more facilities/departments was associated with a visit in the historical visits data and the future appointments data for which the provider was the provider for the visit or appointment; assigning, using the one or more computers, a home facility/department to each of the plurality of providers ("assigned home facility/department") based on the results of calculating; associating for display at an end user device, using the one or more computers, a provider's assigned home facility/department with patient communications data that include patient communications assigned to the provider such that displayable data for the end user device regarding the communications indicates an association between the facility or department and the provider's assigned home facility/department; and sending the displayable data to the end user device.

A twenty-fifth embodiment comprising, the method of the twenty-fourth embodiment further comprising: assigning a dyad relationship, using the one or more computers, between a provider and a staff person using the historical visits data, the dyad relationship associating to associate a support staff person with a provider to associate a support staff person; and using the dyad relationship to associate a support staff person with a current day visit record when the current day visit record does not already include an associated support staff person.

A twenty-sixth embodiment comprising, the method of the twenty-fourth embodiment further comprising: assigning a dyad relationship, using the one or more computers, between a provider and a staff person using the historical visits data, the dyad relationship associating to associate a support staff person with a provider to associate a support staff person; assigning, using the one or more computers, a home facility/department a support staff based on a home facility/department of a provider linked in the dyad relationship to the support staff person ("the support staff person's assigned home facility/department"); associating for display at an end user device, using the one or more computers, the support staff person's assigned home facility/department with patient communications data that include patient communications assigned to the support staff person such that displayable data for the end user device regarding the communications indicates an association between the a particular communication and the provider's assigned home facility/department.

Efficient Computer-Implemented Data Extraction from an Electronic Medical Record System in Support of Health Care Delivery Operational Intelligence A twenty-seventh embodiment comprising, a data extraction method for extracting data in support of intraday management of health care delivery from an electronic medical record ("EMR") system the method comprising: using one or more computers to extract first data sets from one or more computerized data source systems on a first schedule; using one or more computers to extract second sets from one or more computerized data source systems on a second schedule; using at least portions of the first and second to create a plurality of computerized data mart tables accessible by a user interface engine for displaying on a computer intraday medical care delivery information; wherein: the EMR system stores electronic medical records relating to health care delivery to a patient population across an integrated health care enterprise including multiple primary care facilities and one or more hospital facilities, the patient population including at least 50,000 members; the first schedule includes a first extraction frequency of more than once per hour during a least a portion of day and the first extraction frequency is higher than a second extraction frequency of the second schedule; the first data sets includes current day patient visit data extracted from the EMR system; and the second data sets includes patient communications data including at least patient call data and patient electronic message data.

A twenty-eighth embodiment comprising, the data extraction method of the twenty-seventh embodiment wherein the first extraction frequency is at least four times per hour and the second extraction frequency is no less than once per hour.

A twenty-ninth embodiment comprising, the data extraction method of the twenty-seventh embodiment wherein the first extraction frequency is at least six times per hour and the second extraction frequency is no less than once per hour.

A thirtieth embodiment comprising, the data extraction method of the twenty-seventh embodiment wherein the first data set includes a subset of the current day visit data stored by the EMR data system.

A thirty-first embodiment comprising, the data extraction method of the twenty-seventh embodiment wherein the second data set further includes in-patient admission data.

A thirty-second embodiment comprising, the data extraction method of the twenty-seventh embodiment wherein the second data set further includes hospital discharge tracking data.

While the present invention has been particularly described with respect to the illustrated embodiments, it will be appreciated that various alterations, modifications and adaptations may be made based on the present disclosure, and are intended to be within the scope of the present invention. While the invention has been described in connection with what are presently considered to be the most practical and preferred embodiments, it is to be understood that the present invention is not limited to the disclosed embodiments but only by the following claims.

What is claimed is:

1. A computer implemented method for providing health care delivery optimization data to an end user device, the method comprising:

extracting, using a plurality of predetermined extraction frequencies, a plurality of health care delivery data sets from one or more computerized data source systems stored on one or more first computers, the plurality of health care delivery data sets including (i) a first data set including provider data and support staff data, (ii) a second data set including current day visits data related to current day patient visits, the patient visits including data relating a provider and at least one of a department and a facility to a patient visit, (iii) a third data set including historical visits data related to patient visits completed in a previous particular time frame, and (iv) one or more additional data sets including patient communications data related to at least one of patient calls and patient emails and the one or more additional data sets further including future appointments data related to patient appointments in a future particular time frame, wherein the first data set is extracted at a predetermined first extraction frequency, the second data set is extracted at a predetermined second extraction frequency, the third data set is extracted at a predetermined third extraction frequency, and at least one of the one or more additional data sets is extracted at a predetermined fourth extraction frequency, the predetermined second extraction frequency being greater than the predetermined first and third extraction frequencies and being greater than once per hour, the predetermined fourth extraction frequency being greater than once per day but less than the predetermined second extraction frequency; and the predetermined first and third extraction frequencies being less than the predetermined fourth extraction frequency;

receiving and storing, at frequencies corresponding to the predetermined plurality of extraction frequencies, each of the extracted data sets on one or more second computers separate from the one or more first computers; and sending displayable data obtained from the extracted data sets on the one or more second computers to the end user device and causing the displayable data to be displayed on the end user device in response to a user request.

2. The method of claim 1 further comprising:

assigning, using the one or more computers, a dyad relationship between a provider and a support staff person using the historical visits data, wherein at least some of the historical visits data includes data regarding a support staff person performing tasks during a visit; and using the one or more computers to use a dyad relationship to associate a support staff person with a current day visit record when the current day visit record includes a provider but does not already include an associated support staff person.

3. The method of claim 1 further comprising:
assigning, using the one or more computers, a dyad relationship between a provider and a support staff person using the historical visits data, wherein at least some of the historical visits data includes data regarding a support staff person performing tasks during a visit;
assigning, using the one or more computers, a home facility/department to a support staff person based on a home facility/department of a provider linked in a dyad relationship to the support staff person ("the support staff person's assigned home facility/department"); and
associating for display at an end user device, using the one or more computers, the support staff person's assigned home facility/department with patient communications data that include a patient communication assigned to the support staff person such that displayable data for the end user device regarding communications that include the patient communication indicates an association between the communications and the support staff person's assigned home facility/department.

4. The method of claim 1, wherein the patient communications data includes emails initiated by the patient.

5. The method of claim 1, wherein the patient communications data includes phone calls initiated by the patient.

6. The method of claim 3, wherein the patient communications data includes emails initiated by the patient.

7. The method of claim 3, wherein the patient communications data includes phone calls initiated by the patient.

8. A health care support staff management optimization system comprising:
a computer implemented user interface engine communicatively coupled to a data mart on one or more data mart computers separate from one or more first computers and configured to send health care delivery data from the data mart for display by a computerized graphical user interface on an end-user device in response to a request from the end-user device, wherein the health care delivery data includes at least provider data, support staff data, and visits data, the visits data comprising current day visits data and historical visits data;
a computer implemented extraction engine configured to extract, using a plurality of predetermined extraction frequencies, a plurality of health care delivery data sets from one or more computerized data source systems stored on the one or more first computers, the plurality of health care delivery data sets including (i) a first data set including provider data and support staff data, (ii) a second data set including current day visits data related to current day patient visits, the patient visits including data relating a provider and at least one of a department and a facility to a patient visit, (iii) a third data set including historical visits data related to patient visits completed in a previous particular time frame, and (iv) one or more additional data sets including patient communications data related to at least one of patient calls and patient emails and the one or more additional data sets further including future appointments data related to patient appointments in a future particular time frame, wherein the first data set is extracted at a predetermined first extraction frequency, the second data set is extracted at a predetermined second extraction frequency, the third data set is extracted at a predetermined third extraction frequency, and at least one of the one or more additional data sets is extracted at a predetermined fourth extraction frequency, the predetermined second extraction frequency being greater than the predetermined first and third extraction frequencies and being greater than once per hour, the predetermined fourth extraction frequency being greater than once per day but less than the predetermined second extraction frequency; and the predetermined first and third extraction frequencies being less than the predetermined fourth extraction frequency;
a computer implemented data flow engine configured to (i) receive and store, at frequencies corresponding to the plurality of predetermined extraction frequencies, each of the extracted data sets on one or more second computers separate from the one or more first computers, and (ii) use the each of the extracted data sets to populate the data mart.

9. The system of claim 8, wherein the data flow engine is further configured to:
assign, based at least on the plurality of healthcare delivery data sets, each provider to one or more facilities and/or departments ("assigned home facility/department"); and
associate a provider's assigned home facility/department with patient communications data that include a patient communication assigned to the provider;
wherein:
the plurality of health care delivery data sets further includes patient communications data and, such that:
the visits data includes historical visits data and future appointments data; and
at least some of the visits data includes, for each of a plurality of visits or appointments, a provider for the visit or appointment, and a facility/department for the visit or appointment.

10. The system of claim 9, wherein the data flow engine is further configured to:
assign, based on a dyad relationship between a provider and the support staff person based on the historical visits data, a home facility/department to the support staff person based on a home facility/department of a provider linked in the dyad relationship to the support staff person ("the support staff person's assigned home facility/department").

11. The system of claim 8, wherein the patient communications data include at least emails initiated by the patient.

12. The system of claim 8, wherein the patient communications data include at least phone calls initiated by the patient.

13. The computer-implemented method of claim 1 wherein the predetermined first and third extraction frequencies are equal.

14. The computer-implemented method of claim 1 wherein the one or more computerized data source systems stored on one or more first computers include electronic medical records for at least 50,000 different patients.

* * * * *